United States Patent
Bais et al.

(10) Patent No.: US 10,456,470 B2
(45) Date of Patent: Oct. 29, 2019

(54) DIAGNOSTIC METHODS AND COMPOSITIONS FOR TREATMENT OF GLIOBLASTOMA

(71) Applicant: Genentech, Inc., South San Francisco, CA (US)

(72) Inventors: Carlos Bais, South San Francisco, CA (US); Richard Bourgon, South San Francisco, CA (US); Heidi Phillips, South San Francisco, CA (US); Thomas Sandmann, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 364 days.

(21) Appl. No.: 14/471,734

(22) Filed: Aug. 28, 2014

(65) Prior Publication Data

US 2015/0064178 A1    Mar. 5, 2015

Related U.S. Application Data

(60) Provisional application No. 61/872,346, filed on Aug. 30, 2013.

(51) Int. Cl.
| | | |
|---|---|---|
| *A61K 39/00* | (2006.01) | |
| *A61K 39/395* | (2006.01) | |
| *C07K 16/22* | (2006.01) | |
| *C12Q 1/68* | (2018.01) | |
| *C12Q 1/6886* | (2018.01) | |
| *A61K 45/06* | (2006.01) | |
| *G01N 33/574* | (2006.01) | |

(52) U.S. Cl.
CPC ........ *A61K 45/06* (2013.01); *A61K 39/39558* (2013.01); *C07K 16/22* (2013.01); *C12Q 1/6886* (2013.01); *G01N 33/57407* (2013.01); *C12Q 2600/106* (2013.01); *C12Q 2600/158* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,500,362 | A | 3/1996 | Robinson et al. |
| 6,054,297 | A | 4/2000 | Carter et al. |
| 6,582,959 | B2 | 6/2003 | Kim |
| 6,703,020 | B1 | 3/2004 | Thorpe et al. |
| 6,884,879 | B1 | 4/2005 | Baca et al. |
| 7,060,269 | B1 | 6/2006 | Baca et al. |
| 2002/0032315 | A1 | 3/2002 | Baca et al. |
| 2003/0190317 | A1 | 10/2003 | Baca et al. |
| 2003/0203409 | A1 | 10/2003 | Kim |
| 2003/0206899 | A1 | 11/2003 | Ferrara et al. |
| 2005/0186208 | A1 | 8/2005 | Fyfe et al. |
| 2006/0009360 | A1 | 1/2006 | Pifer et al. |
| 2007/0141066 | A1 | 6/2007 | Phillips et al. |
| 2010/0226880 | A1 | 9/2010 | Fyfe et al. |
| 2010/0266589 | A1 | 10/2010 | Hedrick et al. |
| 2011/0206662 | A1 | 8/2011 | Dupont et al. |
| 2013/0216533 | A1 | 8/2013 | Bais et al. |
| 2014/0342924 | A1 | 11/2014 | Harkin et al. |
| 2015/0056190 | A1 | 2/2015 | Hegde et al. |
| 2015/0065781 | A1 | 3/2015 | Bais et al. |
| 2015/0148585 | A1 | 5/2015 | Das et al. |
| 2016/0002732 | A1 | 1/2016 | Harkin et al. |
| 2017/0051360 | A1 | 2/2017 | Bais et al. |

FOREIGN PATENT DOCUMENTS

| | | |
|---|---|---|
| CN | 102575298 A | 7/2012 |
| EP | 0666868 B1 | 4/2002 |
| JP | 2007-526897 A | 9/2007 |
| JP | 2013-520442 A | 6/2013 |
| JP | 2013-536240 A | 9/2013 |
| TW | 201138819 A1 | 11/2011 |
| WO | WO-89/06692 A1 | 7/1989 |
| WO | WO-94/10202 A1 | 5/1994 |
| WO | WO-95/27062 A1 | 10/1995 |
| WO | WO-96/30046 A1 | 10/1996 |
| WO | WO-98/45332 A2 | 10/1998 |
| WO | WO-2005/012359 A2 | 2/2005 |
| WO | WO-2005/016968 A2 | 2/2005 |
| WO | WO-2005/044853 A2 | 5/2005 |
| WO | WO-2007/111733 A2 | 10/2007 |
| WO | WO-2008/109423 A1 | 9/2008 |
| WO | WO-2011/020049 A1 | 2/2011 |
| WO | WO-2011/106300 A2 | 9/2011 |
| WO | WO-2012/027379 A2 | 3/2012 |

(Continued)

OTHER PUBLICATIONS

Yang et al. (2008). Clin. Cancer Res. 14(18):5893-5899.*
Fiebig et al. (2008). Journal of Clinical Oncology. 26:14519.*
Stupp et al., "Radiotherapy plus concomitant and adjuvant temozolomide for glioblastoma," N Engl J Med. 352(10):987-96 (2005).
International Search Report and Written Opinion for International Application No. PCT/US14/53500, dated Feb. 23, 2015 (28 pages).
Carmeliet et al., "Angiogenesis in cancer and other diseases," Nature. 407(6801):249-57 (2000).
Chinot et al., "AVAglio: Phase 3 trial of bevacizumab plus temozolomide and radiotherapy in newly diagnosed glioblastoma multiforme," Adv Ther. 28(4):334-40 (2011).
Chinot et al., "Bevacizumab plus radiotherapy-temozolomide for newly diagnosed glioblastoma," N Engl J Med. 370(8):709-22 (2014).

(Continued)

*Primary Examiner* — Christine J Saoud
*Assistant Examiner* — Jon M Lockard
(74) *Attorney, Agent, or Firm* — Clark & Elbing LLP; Karen L. Elbing

(57) ABSTRACT

The invention provides methods and compositions to detect expression of one or more biomarkers for identifying and treating patients having glioblastomas who are likely to be responsive to VEGF antagonist therapy. The invention also provides kits and articles of manufacture for use in the methods.

14 Claims, 6 Drawing Sheets
(6 of 6 Drawing Sheet(s) Filed in Color)
Specification includes a Sequence Listing.

(56) References Cited

FOREIGN PATENT DOCUMENTS

| WO | WO-2012/167278 A1 | 12/2012 |
|---|---|---|
| WO | WO-2013/106765 A1 | 7/2013 |
| WO | WO-2013/148288 A1 | 10/2013 |
| WO | WO-2014/025813 A1 | 2/2014 |
| WO | WO-2014/087156 A1 | 6/2014 |

OTHER PUBLICATIONS

Cloughsey et al., "Phase III Trial of Bevacizumab Added to Standard Radiotherapy and Temozolomide for Newly Diagnosed Glioblastoma: Final Progression—Free Survival and Preliminary Overall Survival Results from AVAglio (PL02.002)," Neurology. 80(Meeting Abstracts 1):PL02.002 (2013) (2 pages).
Cooper et al., "The proneural molecular signature is enriched in oligodendrogliomas and predicts improved survival among diffuse gliomas," PLoS One. 5(9):e12548 (2010) (9 pages).
Ferrara, "Vascular endothelial growth factor. The trigger for neovascularization in the eye," Lab Invest. 72(6):615-8 (1995).
Friedman et al., "Irinotecan therapy in adults with recurrent or progressive malignant glioma," J Clin Oncol. 17(5):1516-25 (1999).
Gossmann et al., "Dynamic contrast-enhanced magnetic resonance imaging as a surrogate marker of tumor response to anti-angiogenic therapy in a xenograft model of glioblastoma multiforme," J Magn Reson Imaging. 15(3):233-40 (2002).
Hasan et al., "VEGF antagonists," Expert Opin Biol Ther. 1(4):703-18 (2001).
Houck et al., "The vascular endothelial growth factor family: identification of a fourth molecular species and characterization of alternative splicing of RNA," Mol Endocrinol. 5(12):1806-14 (1991).
Lai et al., "Phase II pilot study of bevacizumab in combination with temozolomide and regional radiation therapy for up-front treatment of patients with newly diagnosed glioblastoma multiforme: interim analysis of safety and tolerability," Int J Radiat Oncol Biol Phys. 71(5):1372-80 (2008).
Lai et al., "Phase II study of bevacizumab plus temozolomide during and after radiation therapy for patients with newly diagnosed glioblastoma multiforme," J Clin Oncol. 29(2):142-8 (2011).
Leung et al., "Vascular endothelial growth factor is a secreted angiogenic mitogen," Science. 246(4935):1306-9 (1989).
Macdonald et al., "Response criteria for phase II studies of supratentorial malignant glioma," J Clin Oncol. 8(7):1277-80 (1990).
Matthews et al., "A receptor tyrosine kinase cDNA isolated from a population of enriched primitive hematopoietic cells and exhibiting close genetic linkage to c-kit," Proc Natl Acad Sci U S A. 88(20):9026-30 (1991).
Meyer et al., "A novel vascular endothelial growth factor encoded by Orf virus, VEGF-E, mediates angiogenesis via signalling through VEGFR-2 (KDR) but not VEGFR-1 (Flt-1) receptor tyrosine kinases," EMBO J. 18(2):363-74 (1999).
Muller et al., "VEGF and the Fab fragment of a humanized neutralizing antibody: crystal structure of the complex at 2.4 a resolution and mutational analysis of the interface," Structure. 6(9):1153-67 (1998).
Narayana et al., "A clinical trial of bevacizumab, temozolomide, and radiation for newly diagnosed glioblastoma," J Neurosurg. 116(2):341-5 (2012).
Ogawa et al., "A novel type of vascular endothelial growth factor, VEGF-E (NZ-7 VEGF), preferentially utilizes KDR/Flk-1 receptor and carries a potent mitotic activity without heparin-binding domain," J Biol Chem. 273(47):31273-82 (1998).
Popkov et al., "Human/mouse cross-reactive anti-VEGF receptor 2 recombinant antibodies selected from an immune b9 allotype rabbit antibody library," J Immunol Methods. 288(1-2):149-64 (2004).
Presta et al., "Humanization of an anti-vascular endothelial growth factor monoclonal antibody for the therapy of solid tumors and other disorders," Cancer Res. 57(20):4593-9 (1997).
Schlessinger et al., "Growth factor signaling by receptor tyrosine kinases," Neuron. 9(3):383-91 (1992).
Taphoorn et al., "Health-Related Quality of Life in a Randomized Phase III Study of Bevacizumab, Temozolomide, and Radiotherapy in Newly Diagnosed Glioblastoma," J Clin Oncol. 33(19):2166-75 (2015) (14 pages).
Terman et al., "Identification of a new endothelial cell growth factor receptor tyrosine kinase," Oncogene. 6(9):1677-83 (1991).
Ullrich et al., "Signal transduction by receptors with tyrosine kinase activity," Cell. 61(2):203-12 (1990).
Vredenburgh et al., "Addition of bevacizumab to standard radiation therapy and daily temozolomide is associated with minimal toxicity in newly diagnosed glioblastoma multiforme," Int J Radiat Oncol Biol Phys. 82(1):58-66 (2012).
Wick et al., "Chemotherapie bei Gliomen," Onkologe. 17:44-54 (2011) (English language abstract).
Yarden et al., "Growth factor receptor tyrosine kinases," Annu Rev Biochem. 57:443-78 (1988).
Yu et al., "Interaction between bevacizumab and murine VEGF-A: a reassessment," Invest Ophthalmol Vis Sci. 49(2):522-7 (2008).
International Preliminary Report on Patentability for International Patent Application No. PCT/US2013/053841, dated Feb. 10, 2015 (6 pages).
International Preliminary Report on Patentability for International Patent Application No. PCT/US2014/053463, dated Mar. 1, 2016 (6 pages).
International Preliminary Report on Patentability for International Patent Application No. PCT/US2014/053500, dated Mar. 1, 2016 (14 pages).
International Search Report and Written Opinion for International Patent Application No. PCT/US2013/053841, dated Oct. 25, 2013 (10 pages).
International Search Report and Written Opinion for International Patent Application No. PCT/US2014/053463, dated Dec. 4, 2014 (18 pages).
Office Action for U.S. Appl. No. 11/763,288, dated Apr. 16, 2009 (14 pages).
Office Action for U.S. Appl. No. 14/470,443, dated Jun. 27, 2016 (23 pages).
Gerstner et al., "Anti-vascular endothelial growth factor therapy for malignant glioma," available in PMC Mar. 14, 2016, published in final edited form as: Curr Neurol Neurosci Rep. 9(3):254-62 (2009) (15 pages).
Search Report for Singaporean Patent Application No. 11201601471S, dated Feb. 7, 2017 (4 pages).
Written Opinion for Singaporean Patent Application No. 11201601471S, dated Mar. 3, 2017 (9 pages).
Extended European Search Report for European Patent Application No. 14840968.3, dated Mar. 14, 2017 (8 pages).
Kilickap et al., "Complete remission after bevacizumab plus temozolomide in a patient with recurrent glioblastoma multiforme," Acta Oncol. 51(4):544-6 (2012) (4 pages).
DeLay et al., "Microarray analysis verifies two distinct phenotypes of glioblastomas resistant to antiangiogenic therapy," Clin Cancer Res. 18(10):2930-42 (2012).
Extended European Search Report for European Patent Application No. 14839805.0, dated Jun. 14, 2017 (12 pages).
Oken et al., "Toxicity and response criteria of the Eastern Cooperative Oncology Group," Am J Clin Oncol. 5(6):649-55 (1982).
Sathornsumetee et al., "Tumor angiogenic and hypoxic profiles predict radiographic response and survival in malignant astrocytoma patients treated with bevacizumab and irinotecan," J Clin Oncol. 26(2):271-8 (2008).
Sulman et al., "Molecular predictors of outcome and response to bevacizumab (BEV) based on analysis of RTOG 0825, a phase III trial comparing chemoradiation (CRT) with and without BEV in patients with newly diagnosed glioblastoma (GBM)," J Clin Oncol. 31(suppl): abstract LBA2010 (2013) (2 pages).
Communication pursuant to Rule 164(1) for European Patent Application No. 14839805.0, dated Feb. 17, 2017 (6 pages).
Office Action for U.S. Appl. No. 14/616,505, dated Mar. 8, 2017 (27 pages).
Written Opinion for Singaporean Patent Application No. 11201601404V, dated Dec. 15, 2016 (7 pages).

(56) References Cited

OTHER PUBLICATIONS

"Avastin Improves the Quality of Life of Patients Having the Most Aggressive Form of Brain Tumor," Roche Press Release, published Sep. 30, 2009, retrieved from <http://www.roche.ru/home/prjess-zjentr/news/news-2009-09-30.html> Sep. 8, 2017 (9 pages).
"Discussion: Recent Developments in Giloblastoma Treatment—The Impact of AVAglio Trials on Clinical Practice," Nikkei Medical Online Cancer Experts, retrieved from <http://medical.nikkeibp.co.jp/all/data/cancerex/ar_rd_gbm201303.pdf> on Jun. 16, 2017 (partial English translation included) (16 pages).
"Glioma—From Examination to Diagnosis, Treatment, and Follow-Up—Treatment for Cerebral Edema," Center for Cancer Control and Information Services, National Cancer Center, published Jul. 2012, retrieved from <http://ganjoho.jp/data/public/qa_links/brochure/odjrh3000000ul06-att/118.pdf> on Aug. 8, 2017 (partial English translation included) (29 pages).
"Recent Developments in Glioblastoma Treatment—The Impact of AVAglio Trials on Clinical Practice," Nikkei Medical Oncology, published Apr. 24, 2013, retrieved from <http://medical.nikkeibp.co.jp/inc/all/search/cancer/report/> (partial English translation included) (25 pages).
"Temodar Product Label and Full Prescribing Information," amended Mar. 2005 (31 pages).
Avastin Product Label and Full Prescribing Information, amended Jun. 2006 (36 pages).
Avastin Product Label and Full Prescribing Information, amended May 2012 (28 pages).
Desjardins et al., "Bevacizumab and daily temozolomide for recurrent glioblastoma," Cancer. 118(5):1302-12 (2012).
Gruber et al., "Bevacizumab in combination with radiotherapy plus concomitant and adjuvant temozolomide for newly diagnosed glioblastoma: Update progression-free survival, overall survival, and toxicity," J Clin Oncol. 27:15s Abstract 2017 (2009).
Nagpal et al., "Bevacizumab improves quality of life in patients with recurrent glioblastoma," Chemother Res Pract. 2011: 602812 (2011) (6 pages).
Phillips et al., "Molecular subclasses of high-grade glioma predict prognosis, delineate a pattern of disease progression, and resemble stages in neurogenesis," Cancer Cell. 9(3):157-73 (2006).
Piao et al., "Acquired resistance to anti-VEGF therapy in glioblastoma is associated with a mesenchymal transition," Clin Cancer Res. 19(16):4392-403 (2013).
Sandmann et al., "Patients With Proneural Glioblastoma May Derive Overall Survival Benefit From the Addition of Bevacizumab to First-Line Radiotherapy and Temozolomide: Retrospective Analysis of the AVAglio Trial," J Clin Oncol. 33(25):2735-44 (2015) (12 pages).
Schneider et al. "Gliomas in adults," Dtsch Arztebl Int. 107(45):799-808 (2010) (11 pages).
Verhaak et al., "Integrated genomic analysis identifies clinically relevant subtypes of glioblastoma characterized by abnormalities in PDGFRA, IDH1, EGFR, and NF1," Cancer Cell. 17(1):98-110 (2010).
West et al., "JAMA Oncology Patient Page. Performance Status in Patients with Cancer," JAMA Oncol. 1(7):998 (2015).
Communication pursuant to Article 94(3) for European Patent Application No. 14839805.0, dated Jan. 16, 2018 (4 pages).
International Preliminary Report on Patentability for International Patent Application No. PCT/US2015/040408, dated Jan. 17, 2017 (11 pages).
International Search Report and Written Opinion for International Patent Application No. PCT/US2015/040408, dated Dec. 21, 2015 (19 pages).
Invitation to Pay Additional Fees for International Application No. PCT/US2015/040408, dated Oct. 15, 2015 (8 pages).
Notice of Reasons for Rejection for Japanese Patent Application No. 2015-526648, dated Apr. 10, 2018 (37 pages).
Office Action for U.S. Appl. No. 14/616,505, dated Nov. 3, 2017 (13 pages).
Office Action for U.S. Appl. No. 15/346,164, dated Mar. 9, 2018 (11 pages).
Huse et al., "Survival benefit from bevacizumab in newly diagnosed glioblastoma (GBM) according to transcriptional subclasses." J Clin Oncol Suppl. 31(15):2057 (2013).
Communication Pursuant to Article 94(3) EPC for European Patent Application No. 14 839 805.0, dated Jan. 29, 2019 (3 pages).
English Translation of Search Report for Chinese Patent Application No. 201480053412.X, dated Dec. 3, 2018 (2 pages).
Examination Report for Australian Patent Application No. 2014312079, dated Feb. 5, 2019 (5 pages).
Notification of Defects in Israeli Patent Application No. 244089, dated Jan. 3, 2019 (9 pages).
Substantive Examination for Malaysian Patent Application No. PI 2016000383, dated Feb. 12, 2019 (4 pages).
Written Opinion for Singaporean Patent Application No. 11201601471S, dated Jan. 25, 2019 (6 pages).

* cited by examiner

US 10,456,470 B2

DIAGNOSTIC METHODS AND COMPOSITIONS FOR TREATMENT OF GLIOBLASTOMA

FIELD OF THE INVENTION

The present invention is directed to methods for identifying patients having glioblastomas who will benefit from treatment with a VEGF antagonist, e.g., an anti-VEGF antibody.

BACKGROUND OF THE INVENTION

Gliomas account for 81% of all malignant brain and CNS tumors. Glioblastoma (glioblastoma multiforme (GBM); World Health Organization (WHO) grade IV astrocytoma), in particular, accounts for 60% to 70% of malignant gliomas and remains the most aggressive subtype of glioma. It occurs mostly in adults (median age at diagnosis: 64 years) and its incidence is estimated to be 3.05/100,000 in the United States.

With 1- and 5-year overall survival of 29% and 3%, respectively, the prognosis of glioblastoma remains particularly poor (Central Brain Tumor Registry of the United States (2005) (CBTRUS).

Measuring expression levels of biomarkers can be an effective means to identify patients having glioblastomas that will respond to specific therapies including, e.g., treatment with VEGF antagonists, such as anti-VEGF antibodies.

There is a need for an effective means of determining which patients having glioblastomas will respond to which treatment and for incorporating such determinations into effective treatment regimens for patients with VEGF antagonist therapies, whether used as single agents or combined with other agents.

SUMMARY OF THE INVENTION

The present invention provides methods for identifying patients having glioblastomas who will likely respond to treatment with a VEGF antagonist (e.g., an anti-VEGF antibody, e.g., bevacizumab). These patients are identified based on expression level of at least one of the genes set forth in Table 1, 2, or 3 below.

In a first aspect, the invention provides methods of determining whether a patient having a glioblastoma is likely to respond to treatment with a VEGF antagonist, the methods including: (a) detecting expression of at least one of the genes set forth in Table 1, 2, or 3 (e.g., 1, 2, 3, 4, 5, 6, 7, 8, 9, or 10 of the genes listed in Table 3 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, or 60 or more different genes) listed in Table 2 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100 or more different genes) listed in Table 1) in a biological sample obtained from the patient prior to administration of a VEGF antagonist to the patient; (b) comparing the expression level of the at least one gene to a reference expression level of the at least one gene, wherein a change in the level of expression of the at least one gene in the patient sample relative to the reference level identifies a patient who is likely to respond to treatment with a VEGF antagonist; and (c) informing the patient that they have an increased likelihood of being responsive to treatment with a VEGF antagonist.

In a second aspect, the invention also provides methods of optimizing efficacy of an anti-cancer therapy for a patient having a glioblastoma, the methods including: (a) detecting expression of at least one of the genes set forth in Table 1, 2, or 3 (e.g., 1, 2, 3, 4, 5, 6, 7, 8, 9, or 10 of the genes listed in Table 3 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, or 60 or more different genes) listed in Table 2 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100 or more different genes) listed in Table 1) in a biological sample obtained from the patient prior to administration of a VEGF antagonist to the patient; (b) comparing the expression level of the at least one gene to a reference expression level of the at least one gene, wherein a change in the level of expression of the at least one gene in the patient sample relative to the reference level identifies a patient who is likely to respond to treatment with a VEGF antagonist; and (c) providing a recommendation to the patient that the anti-cancer therapy include a VEGF antagonist.

In the methods described above, the patient can be in a population of patients having glioblastomas and being tested for responsiveness to a VEGF antagonist and the reference level can be the median level of expression of the at least one gene in the population of patients. In other embodiments of these methods, the reference level may be the median level of expression of the at least one gene in patients having glioblastomas and identified as not responding to VEGF antagonist treatment.

In the methods described above, the change in level of expression of the at least one gene in the patient sample can be an increase or a decrease relative to the reference level.

Expression of the at least one gene in the biological sample obtained from the patient can be detected by measuring, for example, mRNA levels and/or plasma protein levels.

The biological sample can be, for example, tumor tissue, such as a tumor tissue biopsy or a blood plasma sample.

These methods of the invention can further include detecting expression of at least two, three, four, or more genes in a biological sample from the patient. In some embodiments, the methods of the invention can further include detecting expression of at least a fourth or at least a third of the genes in a biological sample from the patient.

In the methods described above, the VEGF antagonist can be an anti-VEGF antibody. The anti-VEGF antibody can be, for example, an anti-VEGF antibody that binds the A4.6.1 epitope, bevacizumab, or an anti-VEGF antibody comprises a variable heavy chain (VH) and a variable light chain (VL), wherein said VH has an amino acid sequence of SEQ ID NO: 2 and said VL has an amino acid sequence of SEQ ID NO: 1.

The methods described above can further include a step of administering a VEGF antagonist to the patient. The administered VEGF antagonist can be an anti-VEGF antibody, for example, an anti-VEGF antibody that binds the A4.6.1 epitope, bevacizumab, or an anti-VEGF antibody comprises a variable heavy chain (VH) and a variable light chain (VL), wherein the VH has an amino acid sequence of SEQ ID NO: 2 and the VL has an amino acid sequence of SEQ ID NO: 1.

The methods described above can further include carrying out therapy using (i) an agent selected from the group consisting of an anti-neoplastic agent, a chemotherapeutic agent, a growth inhibitory agent, and a cytotoxic agent, (ii)

radiotherapy, or (iii) a combination thereof. In some embodiments, the methods described above can further include administering a chemotherapeutic agent, such as temozolomide (TMZ), to the patient.

In the methods described above, responsiveness to treatment with a VEGF antagonist can be, for example, an increase in, or extension of, overall survival (OS). In some embodiments, responsiveness to treatment with a VEGF antagonist can be, for example, an increase in, or extension of, progression-free survival (PFS).

In the methods described above, a patient found to be likely to respond to treatment with a VEGF antagonist can have, for example, a glioblastoma of the proneural (PN) type (proneural subtype).

In a third aspect, the invention includes methods of selecting a therapy for a patient having a glioblastoma, the method including: (a) detecting expression of at least one of the genes set forth in Table 1, 2, or 3 (e.g., 1, 2, 3, 4, 5, 6, 7, 8, 9, or 10 of the genes listed in Table 3 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, or 60 or more different genes) listed in Table 2 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100 or more different genes) listed in Table 1) in a biological sample obtained from the patient prior to any administration of a VEGF antagonist to the patient; (b) comparing the expression level of the at least one gene to a reference expression level of the at least one gene, wherein a change in the level of expression of the at least one gene in the patient sample relative to the reference level identifies a patient who is likely to respond to treatment with a VEGF antagonist; and (c) selecting a therapy including a VEGF antagonist if the patient is identified as likely to respond to treatment with a VEGF antagonist and, optionally, recommending to the patient the selected therapy including a VEGF antagonist.

In these methods, the reference level can be the median level of expression of the at least one gene in a population of patients having glioblastomas. In some embodiments of these methods, the reference level can be the median level of expression of the at least one gene in patients having glioblastomas and identified as not responding to VEGF antagonist treatment.

In these methods, the change in level of expression of the at least one gene in the patient sample can be an increase or a decrease relative to the reference level. Expression of the at least one gene in the biological sample obtained from the patient can be detected by measuring, for example, mRNA levels and/or plasma protein levels. The biological sample can be, for example, tumor tissue, such as a tumor tissue biopsy or a blood plasma sample.

These methods of the invention can further include detecting expression of at least two, three, four, or more genes in a biological sample from the patient. In some embodiments of these methods, further detection of the expression of at least a fourth or at least a third of the genes in a biological sample from the patient.

In these methods, the therapy of step (c) can be an agent selected from the group consisting of an anti-neoplastic agent, a chemotherapeutic agent, a growth inhibitory agent, and a cytotoxic agent, radiotherapy, or a combination thereof. In some embodiments, these methods further include administering a chemotherapeutic agent, such as TMZ, to the patient.

These methods can further include the step of (d): administering an effective amount of a VEGF antagonist to the patient if the patient is identified as likely to respond to treatment with a VEGF antagonist. The administered VEGF antagonist can be anti-VEGF antibody, for example, an anti-VEGF antibody that binds the A4.6.1 epitope, bevacizumab, or an anti-VEGF antibody comprises a VH and a VL, wherein the VH has an amino acid sequence of SEQ ID NO: 2 and the VL has an amino acid sequence of SEQ ID NO: 1. In some embodiments, the methods further include administering an effective amount of at least a second agent. The second agent can, for example, be selected from the group consisting of: an anti-neoplastic agent, a chemotherapeutic agent, a growth inhibitory agent, a cytotoxic agent, and combinations thereof. In some embodiments, the second agent is TMZ.

In these methods, responsiveness to treatment with a VEGF antagonist can be, for example, an increase in, or extension of, OS. In some embodiments of these methods, responsiveness to treatment with a VEGF antagonist can be, for example, an increase in, or extension of, PFS.

In these methods, a patient found to be likely to respond to treatment with a VEGF antagonist can have, for example, a glioblastoma of the PN type (PN subtype).

In any of the methods of the first, second, and third aspects, the at least one gene can be selected from the group consisting of NCAM1, OMG, PRKCZ, GALNT13, GPR17, DNM3, FERMT1, SNAP91, ABHD6, and PFN2. When the at least one gene is selected from the group consisting of NCAM1, OMG, PRKCZ, GALNT13, GPR17, DNM3, FERMT1, SNAP91, ABHD6, and PFN2, the change in level of expression of the at least one gene in the patient sample may be an increase relative to the reference level.

In a fourth aspect, the invention provides methods of determining whether a patient having a glioblastoma is likely to respond to treatment with a VEGF antagonist, the methods including: (a) detecting expression of at least one of the genes set forth in Table 1, 2, or 3 (e.g., 1, 2, 3, 4, 5, 6, 7, 8, 9, or 10 of the genes listed in Table 3 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, or 60 or more different genes) listed in Table 2 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100 or more different genes) listed in Table 1) in a biological sample obtained from the patient prior to administration of a VEGF antagonist to the patient, wherein the at least one gene is selected from the group consisting of NCAM1, OMG, PRKCZ, GALNT13, GPR17, DNM3, FERMT1, SNAP91, ABHD6, and PFN2; (b) comparing the expression level of the at least one gene to a reference expression level of the at least one gene, wherein an increase in the level of expression of NCAM1, OMG, PRKCZ, GALNT13, GPR17, DNM3, FERMT1, SNAP91, ABHD6, and/or PFN2 in the patient sample relative to the reference level identifies a patient who is likely to respond to treatment with a VEGF antagonist; and (c) informing the patient that they have an increased likelihood of being responsive to treatment with a VEGF antagonist.

In a fifth aspect, the invention provides methods of optimizing therapeutic efficacy of an anti-cancer therapy for a patient having a glioblastoma, the methods including: (a) detecting expression of at least one of the genes set forth in Table 1, 2, or 3 (e.g., 1, 2, 3, 4, 5, 6, 7, 8, 9, or 10 of the genes listed in Table 3 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, or 60 or more different genes) listed in Table 2 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100 or more different genes) listed in Table 1) in a biological sample obtained from the patient prior to administration of a VEGF antagonist to the patient, wherein the at least one gene is selected from the group consisting of NCAM1, OMG, PRKCZ, GALNT13, GPR17, DNM3, FERMT1, SNAP91, ABHD6, and PFN2; (b) comparing the expression level of the at least one gene to a reference expression level of the at least one gene, wherein an increase in the level of expression of NCAM1, OMG, PRKCZ, GALNT13, GPR17, DNM3, FERMT1, SNAP91, ABHD6, and/or PFN2 in the patient sample relative to the reference level identifies a patient who is likely to respond to treatment with a VEGF antagonist; and (c) providing a recommendation to the patient that the anti-cancer therapy include a VEGF antagonist.

In a sixth aspect, the invention includes methods of selecting a therapy for a patient having a glioblastoma, the method including: (a) detecting expression of at least one of the genes set forth in Table 1, 2, or 3 (e.g., 1, 2, 3, 4, 5, 6, 7, 8, 9, or 10 of the genes listed in Table 3 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, or 60 or more different genes) listed in Table 2 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100 or more different genes) listed in Table 1) in a biological sample obtained from the patient prior to administration of a VEGF antagonist to the patient, wherein the at least one gene is selected from the group consisting of NCAM1, OMG, PRKCZ, GALNT13, GPR17, DNM3, FERMT1, SNAP91, ABHD6, and PFN2; (b) comparing the expression level of the at least one gene to a reference expression level of the at least one gene, wherein an increase in the level of expression of NCAM1, OMG, PRKCZ, GALNT13, GPR17, DNM3, FERMT1, SNAP91, ABHD6, and/or PFN2 in the patient sample relative to the reference level identifies a patient who is likely to respond to treatment with a VEGF antagonist; and (c) selecting a therapy including a VEGF antagonist if the patient is identified as likely to respond to treatment with a VEGF antagonist and, optionally, recommending to the patient the selected therapy including a VEGF antagonist.

In any of the methods of the fourth, fifth, and sixth aspects, the patient can be in a population of patients having glioblastomas and being tested for responsiveness to a VEGF antagonist and the reference level can be the median level of expression of the at least one gene in the population of patients. In other embodiments of these methods, the reference level may be the median level of expression of the at least one gene in patients having glioblastomas and identified as not responding to VEGF antagonist treatment.

In a seventh aspect, the invention provides methods of determining whether a patient having a glioblastoma is likely to respond to treatment with a VEGF antagonist, the methods including: (a) detecting expression of at least one of the genes set forth in Table 1, 2, or 3 (e.g., 1, 2, 3, 4, 5, 6, 7, 8, 9, or 10 of the genes listed in Table 3 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, or 60 or more different genes) listed in Table 2 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100 or more different genes) listed in Table 1) in a biological sample obtained from the patient prior to administration of a VEGF antagonist to the patient; and (b) comparing the expression level of the at least one gene to a reference expression level of the at least one gene, wherein a change in the level of expression of the at least one gene in the patient sample relative to the reference level identifies a patient who is likely to respond to treatment with a VEGF antagonist. In some embodiments, the methods of the seventh aspect can further include informing the patient that they have an increased likelihood of being responsive to treatment with a VEGF antagonist.

In an eighth aspect, the invention also provides methods of optimizing efficacy of an anti-cancer therapy for a patient having a glioblastoma, the methods including: (a) detecting expression of at least one of the genes set forth in Table 1, 2, or 3 (e.g., 1, 2, 3, 4, 5, 6, 7, 8, 9, or 10 of the genes listed in Table 3 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, or 60 or more different genes) listed in Table 2 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100 or more different genes) listed in Table 1) in a biological sample obtained from the patient prior to administration of a VEGF antagonist to the patient; and (b) comparing the expression level of the at least one gene to a reference expression level of the at least one gene, wherein a change in the level of expression of the at least one gene in the patient sample relative to the reference level identifies a patient who is likely to respond to treatment with a VEGF antagonist. In some embodiments, the methods of the eighth aspect can further include providing a recommendation to the patient that the anti-cancer therapy comprise a VEGF antagonist.

In some embodiments of any of the methods of the seventh and eighth aspects, the patient can be in a population of patients having glioblastomas and being tested for responsiveness to a VEGF antagonist and the reference level can be the median level of expression of the at least one gene in the population of patients. In other embodiments of these methods, the reference level may be the median level of expression of the at least one gene in patients having glioblastomas and identified as not responding to VEGF antagonist treatment.

In some embodiments of any of the methods of the seventh and eighth aspects, the change in level of expression of the at least one gene in the patient sample can be an increase or a decrease relative to the reference level.

In some embodiments of any of the methods of the seventh and eighth aspects, expression of the at least one gene in the biological sample obtained from the patient can be detected by measuring, for example, mRNA levels and/or plasma protein levels.

In some embodiments of any of the methods of the seventh and eighth aspects, the biological sample can be, for example, tumor tissue, such as a tumor tissue biopsy or a blood plasma sample.

The methods of the seventh and eighth aspects of the invention can further include detecting expression of at least two, three, four, or more genes in a biological sample from the patient. In some embodiments, the methods of the seventh and eighth aspects of the invention can further include detecting expression of at least a fourth or at least a third of the genes in a biological sample from the patient.

In some embodiments of any of the methods of the seventh and eighth aspects, the VEGF antagonist can be an anti-VEGF antibody. The anti-VEGF antibody can be, for example, an anti-VEGF antibody that binds the A4.6.1 epitope, bevacizumab, or an anti-VEGF antibody comprises a variable heavy chain (VH) and a variable light chain (VL), wherein said VH has an amino acid sequence of SEQ ID NO: 2 and said VL has an amino acid sequence of SEQ ID NO: 1.

The methods of the seventh and eighth aspects of the invention can further include a step of administering a VEGF antagonist to the patient. The administered VEGF antagonist can be anti-VEGF antibody, for example, an anti-VEGF antibody that binds the A4.6.1 epitope, bevacizumab, or an anti-VEGF antibody comprises a variable heavy chain (VH) and a variable light chain (VL), wherein the VH has an amino acid sequence of SEQ ID NO: 2 and the VL has an amino acid sequence of SEQ ID NO: 1.

In some embodiments, any of the methods of the seventh and eighth aspects can further include carrying out therapy using (i) an agent selected from the group consisting of an anti-neoplastic agent, a chemotherapeutic agent, a growth inhibitory agent, and a cytotoxic agent, (ii) radiotherapy, or (iii) a combination thereof. In some embodiments, the methods described above can further include administering a chemotherapeutic agent, such as temozolomide (TMZ), to the patient.

In some embodiments of any of the methods of the seventh and eighth aspects, responsiveness to treatment with a VEGF antagonist can be, for example, an increase in, or extension of, overall survival (OS). In some embodiments, responsiveness to treatment with a VEGF antagonist can be, for example, an increase in, or extension of, progression-free survival (PFS).

In some embodiments of any of the methods of the seventh and eighth aspects, a patient found to be likely to respond to treatment with a VEGF antagonist can have, for example, a glioblastoma of the proneural (PN) type (proneural subtype).

In a ninth aspect, the invention features methods of selecting a therapy for a patient having a glioblastoma, the method including: (a) detecting expression of at least one of the genes set forth in Table 1, 2, or 3 (e.g., 1, 2, 3, 4, 5, 6, 7, 8, 9, or 10 of the genes listed in Table 3 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, or 60 or more different genes) listed in Table 2 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100 or more different genes) listed in Table 1) in a biological sample obtained from the patient prior to any administration of a VEGF antagonist to the patient; and (b) comparing the expression level of the at least one gene to a reference expression level of the at least one gene, wherein a change in the level of expression of the at least one gene in the patient sample relative to the reference level identifies a patient who is likely to respond to treatment with a VEGF antagonist. In some embodiments, the methods of the ninth aspect can further include selecting a therapy including a VEGF antagonist if the patient is identified as likely to respond to treatment with a VEGF antagonist and, optionally, recommending to the patient the selected therapy including a VEGF antagonist.

In some embodiments of the methods of the ninth aspect, the reference level can be the median level of expression of the at least one gene in a population of patients having glioblastomas. In some embodiments of the methods of the ninth aspect, the reference level can be the median level of expression of the at least one gene in patients having glioblastomas and identified as not responding to VEGF antagonist treatment.

In some embodiments of the methods of the ninth aspect, the change in level of expression of the at least one gene in the patient sample can be an increase or a decrease relative to the reference level. Expression of the at least one gene in the biological sample obtained from the patient can be detected by measuring, for example, mRNA levels and/or plasma protein levels. The biological sample can be, for example, tumor tissue, such as a tumor tissue biopsy or a blood plasma sample.

The methods of the ninth aspect of the invention can further include detecting expression of at least two, three, four, or more genes in a biological sample from the patient. In some embodiments of these methods, further detection of the expression of at least a fourth or at least a third of the genes in a biological sample from the patient.

In some embodiments of the methods of the ninth aspect, the therapy of step (d) can be an agent selected from the group consisting of an anti-neoplastic agent, a chemotherapeutic agent, a growth inhibitory agent, and a cytotoxic agent, radiotherapy, or a combination thereof. In some embodiments, these methods further include administering a chemotherapeutic agent, such as TMZ, to the patient.

The methods of the ninth aspect of the invention can further include the step of (e): administering an effective amount of a VEGF antagonist to the patient if the patient is identified as likely to respond to treatment with a VEGF antagonist. The administered VEGF antagonist can be an anti-VEGF antibody, for example, an anti-VEGF antibody that binds the A4.6.1 epitope, bevacizumab, or an anti-VEGF antibody comprises a VH and a VL, wherein the VH has an amino acid sequence of SEQ ID NO: 2 and the VL has an amino acid sequence of SEQ ID NO: 1.

In some embodiments of the methods of the ninth aspect, the methods further include administering an effective amount of at least a second agent. The second agent can, for example, be selected from the group consisting of: an anti-neoplastic agent, a chemotherapeutic agent, a growth inhibitory agent, a cytotoxic agent, and combinations thereof. In some embodiments, the second agent is TMZ.

In some embodiments of the methods of the ninth aspect, responsiveness to treatment with a VEGF antagonist can be, for example, an increase in, or extension of, OS. In some embodiments of these methods, responsiveness to treatment with a VEGF antagonist can be, for example, an increase in, or extension of, PFS.

In some embodiments of the methods of the ninth aspect, a patient found to be likely to respond to treatment with a VEGF antagonist can have, for example, a glioblastoma of the PN type (PN subtype).

In any of the methods of the seventh, eighth, and ninth aspects, the at least one gene can be selected from the group consisting of NCAM1, OMG, PRKCZ, GALNT13, GPR17, DNM3, FERMT1, SNAP91, ABHD6, and PFN2. When the at least one gene is selected from the group consisting of NCAM1, OMG, PRKCZ, GALNT13, GPR17, DNM3, FERMT1, SNAP91, ABHD6, and PFN2, the change in level of expression of the at least one gene in the patient sample may be an increase relative to the reference level.

In a tenth aspect, the invention provides methods of determining whether a patient having a glioblastoma is likely to respond to treatment with a VEGF antagonist, the methods including: (a) detecting expression of at least one of the genes set forth in Table 1, 2, or 3 (e.g., 1, 2, 3, 4, 5, 6, 7, 8, 9, or 10 of the genes listed in Table 3 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, or 60 or more different genes) listed in Table 2 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100 or more different genes) listed in Table 1) in a biological sample obtained from the patient prior to administration of a VEGF antagonist to the patient, wherein the at least one gene is selected from the group consisting of NCAM1, OMG, PRKCZ, GALNT13, GPR17, DNM3, FERMT1, SNAP91, ABHD6, and PFN2; and (b) comparing the expression level of the at least one gene to a reference expression level of the at least one gene, wherein an increase in the level of expression of NCAM1, OMG, PRKCZ, GALNT13, GPR17, DNM3, FERMT1, SNAP91, ABHD6, and/or PFN2 in the patient sample relative to the reference level identifies a patient who is likely to respond to treatment with a VEGF antagonist.

In an eleventh aspect, the invention provides methods of optimizing therapeutic efficacy of an anti-cancer therapy for a patient having a glioblastoma, the methods including: (a) detecting expression of at least one of the genes set forth in Table 1, 2, or 3 (e.g., 1, 2, 3, 4, 5, 6, 7, 8, 9, or 10 of the genes listed in Table 3 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, or 60 or more different genes) listed in Table 2 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100 or more different genes) listed in Table 1) in a biological sample obtained from the patient prior to administration of a VEGF antagonist to the patient, wherein the at least one gene is selected from the group consisting of NCAM1, OMG, PRKCZ, GALNT13, GPR17, DNM3, FERMT1, SNAP91, ABHD6, and PFN2; and (b) comparing the expression level of the at least one gene to a reference expression level of the at least one gene, wherein an increase in the level of expression of NCAM1, OMG, PRKCZ, GALNT13, GPR17, DNM3, FERMT1, SNAP91, ABHD6, and/or PFN2 in the patient sample relative to the reference level identifies a patient who is likely to respond to treatment with a VEGF antagonist.

In a twelfth aspect, the invention includes methods of selecting a therapy for a patient having a glioblastoma, the method including: (a) detecting expression of at least one of the genes set forth in Table 1, 2, or 3 (e.g., 1, 2, 3, 4, 5, 6, 7, 8, 9, or 10 of the genes listed in Table 3 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, or 60 or more different genes) listed in Table 2 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100 or more different genes) listed in Table 1) in a biological sample obtained from the patient prior to administration of a VEGF antagonist to the patient, wherein the at least one gene is selected from the group consisting NCAM1, OMG, PRKCZ, GALNT13, GPR17, DNM3, FERMT1, SNAP91, ABHD6, and PFN2; and (b) comparing the expression level of the at least one gene to a reference expression level of the at least one gene, wherein an increase in the level of expression of NCAM1, OMG, PRKCZ, GALNT13, GPR17, DNM3, FERMT1, SNAP91, ABHD6, and/or PFN2 in the patient sample relative to the reference level identifies a patient who is likely to respond to treatment with a VEGF antagonist.

In any of the methods of the tenth, eleventh, and twelfth aspects, the patient can be in a population of patients having glioblastomas and being tested for responsiveness to a VEGF antagonist and the reference level can be the median level of expression of the at least one gene in the population of patients. In other embodiments of these methods, the reference level may be the median level of expression of the at least one gene in patients having glioblastomas and identified as not responding to VEGF antagonist treatment.

In another aspect, the invention features a kit for determining whether a patient may benefit from treatment with a VEGF antagonist, the kit including: (a) polypeptides or polynucleotides capable of determining the expression level of at least one of the genes set forth in Table 1, 2, or 3 (e.g., 1, 2, 3, 4, 5, 6, 7, 8, 9, or 10 of the genes listed in Table 3 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, or 60 or more different genes) listed in Table 2 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100 or more different genes) listed in Table 1); and (b) instructions for use of the polypeptides or polynucleotides to determine the expression level of at least one of the genes set forth in Table 1, 2, or 3, wherein a change in the level of expression of the at least one gene relative to a reference level indicates that the patient may benefit from treatment with a VEGF antagonist.

BRIEF DESCRIPTION OF THE DRAWINGS

The application file contains at least one drawing executed in color. Copies of this patent or patent application with color drawings will be provided by the Office upon request and payment of the necessary fee.

DETAILED DESCRIPTION OF EMBODIMENTS OF THE INVENTION

I. Introduction

Figure 1:
FIG. 1 is heatmap showing the results of the unsupervised analysis (PAM clustering) of the AvaGlio samples into k=3 groups according to the expression of the extended 108 classifiers genes. Samples assigned with a negative Silhouette width were labeled "Unclassified." Row annotation highlights the signature genes. Column annotation indicates the PAM clusters/gene expression subtype assignment for the samples.

The present invention provides methods and compositions for monitoring and/or identifying patients having glioblastomas whom are sensitive or responsive to treatment with VEGF antagonists, e.g., an anti-VEGF antibody. The invention is based on the discovery that determination of expression levels of at least 1, 2, 3, 4, 5, 6, 7, 8, 9, or 10 or more gene(s) set forth in Table 1, 2, or 3 before treatment with a VEGF antagonist (such as an anti-VEGF antibody) is useful for identifying patients sensitive to or responsive to treatment with a VEGF antagonist, e.g., an anti-VEGF antibody. Optionally, VEGF antagonist therapy can then be selected for the patients and, further, VEGF antagonist therapy can optionally be administered to the patients.

II. Definitions

An "anti-angiogenesis agent" or "angiogenesis inhibitor" refers to a small molecular weight substance, a polynucleotide, a polypeptide, an isolated protein, a recombinant protein, an antibody, or conjugates or fusion proteins thereof, that inhibits angiogenesis, vasculogenesis, or undesirable vascular permeability, either directly or indirectly. It should be understood that the anti-angiogenesis agent includes those agents that bind and block the angiogenic activity of the angiogenic factor or its receptor. For example, an anti-angiogenesis agent is an antibody or other antagonist to an angiogenic agent as defined throughout the specification or known in the art, e.g., but are not limited to, antibodies to VEGF-A or to the VEGF-A receptor (e.g., KDR receptor or Flt-1 receptor), VEGF-trap, anti-PDGFR inhibitors such as Gleevec™ (Imatinib Mesylate). Antiangiogensis agents also include native angiogenesis inhibitors, e.g., angiostatin, endostatin, etc. See, e.g., Klagsbrun and D'Amore, Annu. Rev. Physiol., 53:217-39 (1991); Streit and Detmar, Oncogene, 22:3172-3179 (2003) (e.g., Table 3 listing anti-angiogenic therapy in malignant melanoma); Ferrara & Alitalo, Nature Medicine 5:1359-1364 (1999); Tonini et al., Oncogene, 22:6549-6556 (2003) (e.g., Table 2 listing known antiangiogenic factors); and Sato. Int. J. Clin. Oncol., 8:200-206 (2003) (e.g., Table 1 lists anti-angiogenic agents used in clinical trials).

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

The term "VEGF" or "VEGF-A" is used to refer to the 165-amino acid human vascular endothelial cell growth factor and related 121-, 145-, 189-, and 206-amino acid human vascular endothelial cell growth factors, as described by, e.g., Leung et al. Science, 246:1306 (1989), and Houck et al. Mol. Endocrin., 5:1806 (1991), together with the naturally occurring allelic and processed forms thereof. VEGF-A is part of a gene family including VEGF-B, VEGF-C, VEGF-D, VEGF-E, VEGF-F, and PIGF. VEGF-A primarily binds to two high affinity receptor tyrosine kinases, VEGFR-1 (Flt-1) and VEGFR-2 (Flk-1/KDR), the latter being the major transmitter of vascular endothelial cell mitogenic signals of VEGF-A. Additionally, neuropilin-1 has been identified as a receptor for heparin-binding VEGF-A isoforms, and may play a role in vascular development. The term "VEGF" or "VEGF-A" also refers to VEGFs from non-human species such as mouse, rat, or primate. Sometimes the VEGF from a specific species is indicated by terms such as hVEGF for human VEGF or mVEGF for murine VEGF. Typically, VEGF refers to human VEGF. The term "VEGF" is also used to refer to truncated forms or fragments of the polypeptide comprising amino acids 8 to 109 or 1 to 109 of the 165-amino acid human vascular endothelial cell growth factor. Reference to any such forms of VEGF may be identified in the application, e.g., by "VEGF (8-109)," "VEGF (1-109)" or "VEGF165." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF.

An "anti-VEGF antibody" is an antibody that binds to VEGF with sufficient affinity and specificity. The antibody selected will normally have a binding affinity for VEGF, for example, the antibody may bind hVEGF with a Kd value of between 100 nM-1 pM. Antibody affinities may be determined by a surface plasmon resonance based assay (such as the BIAcore assay as described in PCT Application Publication No. WO2005/012359); enzyme-linked immunoabsorbent assay (ELISA); and competition assays (e.g. RIA's), for example. In certain embodiments, the anti-VEGF antibody of the invention can be used as a therapeutic agent in targeting and interfering with diseases or conditions wherein the VEGF activity is involved. Also, the antibody may be subjected to other biological activity assays, e.g., in order to evaluate its effectiveness as a therapeutic. Such assays are known in the art and depend on the target antigen and intended use for the antibody. Examples include the HUVEC inhibition assay; tumor cell growth inhibition assays (as described in WO 89/06692, for example); antibody-dependent cellular cytotoxicity (ADCC) and complement-mediated cytotoxicity (CDC) assays (U.S. Pat. No. 5,500,362); and agonistic activity or hematopoiesis assays (see WO 95/27062). An anti-VEGF antibody will usually not bind to other VEGF homologues such as VEGF-B or VEGF-C, nor other growth factors such as PIGF, PDGF or bFGF.

A "B20 series antibody" according to this invention is an anti-VEGF antibody that is derived from a sequence of the B20 antibody or a B20-derived antibody according to any one of FIGS. 27-29 of PCT Publication No. WO2005/012359, the entire disclosure of which is expressly incorporated herein by reference. See also PCT Publication No. WO2005/044853, and U.S. Patent Application 60/991,302, the content of these patent applications are expressly incorporated herein by reference. In one embodiment, the B20 series antibody binds to a functional epitope on human VEGF comprising residues F17, M18, D19, Y21, Y25, Q89, I91, K101, E103, and C104.

A "G6 series antibody" according to this invention, is an anti-VEGF antibody that is derived from a sequence of a G6 antibody or G6-derived antibody according to any one of FIGS. 7, 24-26, and 34-35 of PCT Publication No. WO2005/012359, the entire disclosure of which is expressly incorporated herein by reference. See also PCT Publication No. WO2005/044853, the entire disclosure of which is expressly incorporated herein by reference. In one embodiment, the G6 series antibody binds to a functional epitope on human VEGF comprising residues F17, Y21, Q22, Y25, D63, I83 and Q89.

The anti-VEGF antibody "Bevacizumab (BV or Bev)," also known as "rhuMAb VEGF," or "Avastin®", is a recombinant humanized anti-VEGF monoclonal antibody generated according to Presta et al., Cancer Res. 57:4593-4599 (1997). It comprises mutated human IgG1 framework regions and antigen-binding complementarity-determining regions from the murine anti-hVEGF monoclonal antibody A.4.6.1 that blocks binding of human VEGF to its receptors. Approximately 93% of the amino acid sequence of Bevacizumab, including most of the framework regions, is derived from human IgG1, and about 7% of the sequence is derived from the murine antibody A4.6.1. Bevacizumab has a molecular mass of about 149,000 Daltons and is glycosylated. Other anti-VEGF antibodies include the antibodies described in U.S. Pat. No. 6,884,879 and WO 2005/044853.

The "epitope A4.6.1" refers to the epitope recognized by the anti-VEGF antibody bevacizumab (AVASTIN®) (see Muller et al. Structure. 6: 1153-1167, 1998). In certain embodiments of the invention, the anti-VEGF antibodies include, but are not limited to, a monoclonal antibody that binds to the same epitope as the monoclonal anti-VEGF antibody A4.6.1 produced by hybridoma ATCC HB 10709; a recombinant humanized anti-VEGF monoclonal antibody generated according to Presta et al. (Cancer Res. 57: 4593-4599, 1997).

A "functional epitope" according to this invention refers to amino acid residues of an antigen that contribute energetically to the binding of an antibody. Mutation of any one of the energetically contributing residues of the antigen (for example, mutation of wild-type VEGF by alanine or homolog mutation) will disrupt the binding of the antibody such that the relative affinity ratio (IC50 mutant VEGF/IC50 wild-type VEGF) of the antibody will be greater than 5 (see Example 2 of WO2005/012359). In one embodiment, the relative affinity ratio is determined by a solution binding phage displaying ELISA. Briefly, 96-well Maxisorp immunoplates (NUNC) are coated overnight at 4° C. with an Fab form of the antibody to be tested at a concentration of 2 μg/ml in PBS, and blocked with PBS, 0.5% BSA, and 0.05% Tween20 (PBT) for 2 h at room temperature. Serial dilutions of phage displaying hVEGF alanine point mutants (residues 8-109 form) or wild type hVEGF (8-109) in PBT are first incubated on the Fab-coated plates for 15 min at room temperature, and the plates are washed with PBS, 0.05% Tween20 (PBST). The bound phage is detected with an anti-M13 monoclonal antibody horseradish peroxidase (Amersham Pharmacia) conjugate diluted 1:5000 in PBT, developed with 3,3',5,5'-tetramethylbenzidine (TMB, Kirkegaard & Perry Labs, Gaithersburg, Md.) substrate for approximately 5 min, quenched with 1.0 M H3PO4, and read spectrophotometrically at 450 nm. The ratio of 1050 values (1050, ala/IC50, wt) represents the fold of reduction in binding affinity (the relative binding affinity).

The anti-VEGF antibody Ranibizumab or the LUCENTIS® antibody or rhuFab V2 is a humanized, affinity-matured anti-human VEGF Fab fragment. Ranibizumab is produced by standard recombinant technology methods in *Escherichia coli* expression vector and bacterial fermentation. Ranibizumab is not glycosylated and has a molecular mass of 48,000 daltons. See WO 98/45331 and US 2003/0190317.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light-chain and heavy chain variable domains.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al., *Cellular and Mol. Immunology*, 4th ed. (W. B. Saunders, Co., 2000). An antibody may be part of a larger fusion molecule, formed by covalent or non-covalent association of the antibody with one or more other proteins or peptides.

The terms "full-length antibody," "intact antibody," and "whole antibody" are used herein interchangeably to refer to an antibody in its substantially intact form, not antibody fragments as defined below. The terms particularly refer to an antibody with heavy chains that contain an Fc region.

"Antibody fragments" comprise a portion of an intact antibody, preferably comprising the antigen-binding region thereof. Examples of antibody fragments include Fab, Fab', $F(ab')_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields a $F(ab')_2$ fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody-hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

"Single-chain Fv" or "scFv" antibody fragments comprise the VH and VL domains of an antibody, wherein these domains are present in a single polypeptide chain. Generally, the scFv polypeptide further comprises a polypeptide linker between the VH and VL domains that enables the scFv to form the desired structure for antigen binding. For a review of scFv, see, e.g., Pluckthün, in *The Pharmacology of Monoclonal Antibodies*, vol. 113, Rosenburg and Moore eds. (Springer-Verlag, New York: 1994), pp 269-315.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., *Nat. Med.* 9:129-134 (2003); and Hollinger et al., *PNAS USA* 90: 6444-6448 (1993). Triabodies and tetrabodies are also described in Hudson et al., *Nat. Med.* 9:129-134 (2003).

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target-binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal-antibody preparation is directed against a single determinant on an antigen. In addition to their specificity, monoclonal-antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein., *Nature* 256:495-497 (1975); Hongo et al., *Hybridoma* 14 (3):253-260 (1995), Harlow et al., *Antibodies: A Laboratory Manual*, (Cold Spring Harbor Laboratory Press, 2$^{nd}$ ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature* 352:624-628 (1991); Marks et al., *J. Mol. Biol.* 222:581-597 (1992); Sidhu et al., *J. Mol. Biol.* 338(2):299-310 (2004); Lee et al., *J. Mol. Biol.* 340(5):1073-1093 (2004); Fellouse, *PNAS USA* 101(34): 12467-12472 (2004); and Lee et al., *J. Immunol. Methods* 284(1-2):119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *PNAS USA* 90: 2551 (1993); Jakobovits et al., *Nature* 362: 255-258 (1993); Bruggemann et al., *Year in Immunol.* 7:33 (1993); U.S. Pat. Nos. 5,545, 807; 5,545,806; 5,569,825; 5,625,126; 5,633,425; and 5,661,016; Marks et al., *Bio/Technology* 10:779-783 (1992); Lonberg et al., *Nature* 368:856-859 (1994); Morrison, *Nature* 368:812-813 (1994); Fishwild et al., *Nature Biotechnol.* 14:845-851 (1996); Neuberger, *Nature Biotechnol.* 14:826 (1996); and Lonberg and Huszar, *Intern. Rev. Immunol.* 13:65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (e.g., U.S. Pat. No. 4,816,567 and Morrison et al., *PNAS USA* 81:6851-6855 (1984)). Chimeric antibodies include PRIMATIZED® antibodies wherein the antigen-binding region of the antibody is derived from an antibody produced by, e.g., immunizing macaque monkeys with the antigen of interest.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all, or substantially all, of the FRs are those of a human immunoglobulin sequence. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, for example, Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.* 227: 381 (1991); Marks et al., *J. Mol. Biol.* 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.* 147(1):86-95 (1991). See also van Dijk and van de Winkel, *Curr. Opin. Pharmacol.* 5:368-374 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *PNAS USA* 103: 3557-3562 (2006) regarding human antibodies generated via a human B-cell hybridoma technology.

The term "hypervariable region," "HVR," or "HV," when used herein refers to the regions of an antibody-variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993) and Sheriff et al., *Nature Struct. Biol.* 3:733-736 (1996).

A number of HVR delineations are in use and are encompassed herein. The HVRs that are Kabat complementarity-determining regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk, *J. Mol. Biol.* 196:901-917 (1987)). The AbM HVRs represent a compromise between the Kabat CDRs and Chothia structural loops, and are used by Oxford Molecular's AbM antibody-modeling software. The "contact" HVRs are based on an analysis of the available complex crystal structures. The residues from each of these HVRs are noted below.

| Loop | Kabat | AbM | Chothia | Contact | |
|------|-------|-----|---------|---------|---|
| L1 | L24-L34 | L24-L34 | L26-L32 | L30-L36 | |
| L2 | L50-L56 | L50-L56 | L50-L52 | L46-L55 | |
| L3 | L89-L97 | L89-L97 | L91-L96 | L89-L96 | |
| H1 | H31-H35B | H26-H35B | H26-H32 | H30-H35B | (Kabat Numbering) |

| Loop | Kabat | AbM | Chothia | Contact | |
|------|-------|-----|---------|---------|---|
| H1 | H31-H35 | H26-H35 | H26-H32 | H30-H35 | (Chothia Numbering) |
| H2 | H50-H65 | H50-H58 | H53-H55 | H47-H58 | |
| H3 | H95-H102 | H95-H102 | H96-H101 | H93-H101 | |

HVRs may comprise "extended HVRs" as follows: 24-36 or 24-34 (L1), 46-56 or 50-56 (L2), and 89-97 or 89-96 (L3) in the VL, and 26-35 (H1), 50-65 or 49-65 (H2), and 93-102, 94-102, or 95-102 (H3) in the VH. The variable-domain residues are numbered according to Kabat et al., supra, for each of these extended-HVR definitions.

"Framework" or "FR" residues are those variable-domain residues other than the HVR residues as herein defined.

The expression "variable-domain residue-numbering as in Kabat" or "amino acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g., residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

An "affinity-matured" antibody is one with one or more alterations in one or more HVRs thereof which result in an improvement in the affinity of the antibody for antigen, compared to a parent antibody which does not possess those alteration(s). In one embodiment, an affinity-matured antibody has nanomolar or even picomolar affinities for the target antigen. Affinity-matured antibodies are produced by procedures known in the art. For example, Marks et al., *Bio/Technology* 10:779-783 (1992) describes affinity maturation by VH- and VL-domain shuffling. Random mutagenesis of HVR and/or framework residues is described by, for example: Barbas et al., *Proc Nat. Acad. Sci. USA* 91:3809-3813 (1994); Schier et al., *Gene* 169:147-155 (1995); Yelton et al., *J. Immunol.* 155:1994-2004 (1995); Jackson et al., *J. Immunol.* 154(7):3310-3319 (1995); and Hawkins et al., *J. Mol. Biol.* 226:889-896 (1992).

"Antagonists" as used herein refer to compounds or agents which inhibit or reduce the biological activity of the molecule to which they bind. Antagonists include antibodies, synthetic or native-sequence peptides, immunoadhesins, and small-molecule antagonists that bind to VEGF, optionally conjugated with or fused to another molecule. A "blocking" antibody or an "antagonist" antibody is one which inhibits or reduces biological activity of the antigen it binds.

A "VEGF antagonist" refers to a molecule capable of neutralizing, blocking, inhibiting, abrogating, reducing or interfering with VEGF activities including its binding to VEGF or one or more VEGF receptors or the nucleic acid encoding them. Preferably, the VEGF antagonist binds VEGF or a VEGF receptor. VEGF antagonists include anti-VEGF antibodies and antigen-binding fragments thereof, polypeptides that bind VEGF and VEGF receptors and block ligand-receptor interaction (e.g., immunoadhesins, peptibodies), anti-VEGF receptor antibodies and VEGF receptor antagonists such as small molecule inhibitors of the VEGFR tyrosine kinases, aptamers that bind VEGF and nucleic acids that hybridize under stringent conditions to nucleic acid sequences that encode VEGF or VEGF receptor (e.g., RNAi). According to one preferred embodiment, the VEGF antagonist binds to VEGF and inhibits VEGF-induced endothelial cell proliferation in vitro. According to one preferred embodiment, the VEGF antagonist binds to VEGF or a VEGF receptor with greater affinity than a non-VEGF or non-VEGF receptor. According to one preferred embodiment, the VEGF antagonist binds to VEGF or a VEGF receptor with a Kd of between 1 uM and 1 pM. According to another preferred embodiment, the VEGF antagonist binds to VEGF or a VEGF receptor between 500 nM and 1 pM.

According to a preferred embodiment, the VEGF antagonist is selected from a polypeptide such as an antibody, a peptibody, an immunoadhesin, a small molecule or an aptamer. In a preferred embodiment, the antibody is an anti-VEGF antibody such as the AVASTIN® antibody or an anti-VEGF receptor antibody such as an anti-VEGFR2 or an anti-VEGFR3 antibody. Other examples of VEGF antagonists include: VEGF-Trap, Mucagen, PTK787, SU11248, AG-013736, Bay 439006 (sorafenib), ZD-6474, CP632, CP-547632, AZD-2171, CDP-171, SU-14813, CHIR-258, AEE-788, SB786034, BAY579352, CDP-791, EG-3306, GW-786034, RWJ-417975/CT6758 and KRN-633.

The term "anti-neoplastic composition" or "anti-cancer composition" or "anti-cancer agent" refers to a composition useful in treating cancer comprising at least one active therapeutic agent, e.g., "anti-cancer agent." Examples of therapeutic agents (anti-cancer agents) include, but are limited to, e.g., chemotherapeutic agents, growth inhibitory agents, cytotoxic agents, agents used in radiation therapy, anti-angiogenesis agents, apoptotic agents, anti-tubulin agents, and other-agents to treat cancer, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib (Tarceva™), platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA VEGF, or VEGF receptor(s), TRAIL/Apo2, and other bioactive and organic chemical agents, etc. Combinations thereof are also included in the invention.

A "chemotherapeutic agent" is a chemical compound useful in the treatment of cancer. Examples of chemotherapeutic agents include is a chemical compound useful in the treatment of cancer. Examples of chemotherapeutic agents include alkylating agents, such as, for example, temozolomide (TMZ), the imidazotetrazine derivative of the alkylating agent dacarbazine. Additional examples of chemotherapeutics agents include, e.g., paclitaxel or topotecan or pegylated liposomal doxorubicin (PLD). Other examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin; bryostatin; callystatin; CC-1065 (including its adozelesin, carzelesin and bizelesin synthetic analogues);

cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRI-AMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® docetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "growth inhibitory agent" when used herein refers to a compound or composition which inhibits growth and/or proliferation of a cell (e.g., a cell expressing Robo4) either in vitro or in vivo. Thus, the growth inhibitory agent may be one which significantly reduces the percentage of Robo4-expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as the anthracycline antibiotic doxorubicin ((8S-cis)-10-[(3-amino-2,3,6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione), epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

The terms "biomarker" and "marker" are used interchangeably herein to refer to a DNA, RNA, protein, carbohydrate, or glycolipid-based molecular marker, the expression or presence of which in a subject's or patient's sample can be detected by standard methods (or methods disclosed herein) and is useful for monitoring the responsiveness or sensitivity of a mammalian subject to a VEGF antagonist. Such biomarkers include, but are not limited to, the genes set forth in Tables 1, 2, and 3. Expression of such a biomarker may be determined to be higher or lower in a sample obtained from a patient sensitive or responsive to a VEGF antagonist than a reference level (including, e.g., the median expression level of the biomarker in a sample from a group/population of patients, e.g., patients having glioblastomas, and being tested for responsiveness to a VEGF antagonist; the median expression level of the biomarker in a sample from a group/population of patients, e.g., patients having glioblastomas, and identified as not responding to VEGF antagonist treatment; the level in a sample previously obtained from the individual at a prior time; or the level in a sample from a patient who received prior treatment with a VEGF antagonist (such as an anti-VEGF antibody) in a primary tumor setting, and who now may be experiencing metastasis). Individuals having an expression level that is greater than or less than the reference expression level of at least one gene, such as those set forth in Tables 1, 2, and 3, can be identified as subjects/patients likely to respond to treatment with a VEGF antagonist. For example, such subjects/patients who exhibit gene expression levels at the most extreme 50%, 45%, 40%, 35%, 30%, 25%, 20%, 15%, 10%, or 5% relative to (i.e., higher or lower than) the reference level (such as the median level, noted above), can be identified as subjects/patients (e.g., patients having glioblastomas) likely to respond to treatment with a VEGF antagonist, such as an anti-VEGF antibody.

The terms "level of expression" or "expression level" are used interchangeably and generally refer to the amount of a polynucleotide or an amino acid product or protein in a biological sample. "Expression" generally refers to the process by which gene-encoded information is converted into the structures present and operating in the cell. Therefore, according to the invention "expression" of a gene may refer to transcription into a polynucleotide, translation into a protein, or even posttranslational modification of the protein. Fragments of the transcribed polynucleotide, the translated protein, or the post-translationally modified protein shall also be regarded as expressed whether they originate from a transcript generated by alternative splicing or a degraded transcript, or from a post-translational processing of the protein, e.g., by proteolysis. "Expressed genes" include those that are transcribed into a polynucleotide as mRNA and then translated into a protein, and also those that are transcribed into RNA but not translated into a protein (for example, transfer and ribosomal RNAs).

The terms "sample" and "biological sample" are used interchangeably to refer to any biological sample obtained from an individual including body fluids, body tissue (e.g., tumor tissue), cells, or other sources. Body fluids are, e.g., lymph, sera, whole fresh blood, peripheral blood mononuclear cells, frozen whole blood, plasma (including fresh or frozen), urine, saliva, semen, synovial fluid and spinal fluid. Samples also include breast tissue, renal tissue, colonic tissue, brain tissue, muscle tissue, synovial tissue, skin, hair follicle, bone marrow, and tumor tissue. Methods for obtaining tissue biopsies and body fluids from mammals are well known in the art.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, increasing overall survival (OS), increasing progression-free survival (PFS), decreasing the rate of disease progression, amelioration or palliation of the disease state, and remission or improved prognosis.

The phrase "informing the patient" or "providing a recommendation to the patient," with respect to a treatment, as used herein, refers to using the information or data generated relating to the level or presence of at least one of the genes set forth in Table 1, 2, or 3 in a sample of a patient to identify the patient as suitably treated or not suitably treated with a therapy. In some embodiment the therapy may comprise a VEGF antagonist (e.g., an anti-VEGF antibody, e.g., bevacizumab). In some embodiments the recommendation may include the identification of a patient who requires adaptation of an effective amount of a VEGF antagonist (e.g., an anti-VEGF antibody, e.g., bevacizumab) being administered. In some embodiments, recommending a treatment includes recommending that the amount of VEGF antagonist (e.g., an anti-VEGF antibody, e.g., bevacizumab) being administered is adapted. The phrase "informing the patient" or "providing a recommendation," with respect to a treatment, as used herein also may refer to using the information or data generated for proposing or selecting a therapy comprising a VEGF antagonist (e.g., an anti-VEGF antibody, e.g., bevacizumab) for a patient identified or selected as more or less likely to respond to the therapy comprising a VEGF antagonist. The information or data used or generated may be in any form, written, oral or electronic. In some embodiments, using the information or data generated includes communicating, presenting, reporting, storing, sending, transferring, supplying, transmitting, dispensing, or combinations thereof. In some embodiments, communicating, presenting, reporting, storing, sending, transferring, supplying, transmitting, dispensing, or combinations thereof are performed by a computing device, analyzer unit or combination thereof. In some further embodiments, communicating, presenting, reporting, storing, sending, transferring, supplying, transmitting, dispensing, or combinations thereof are performed by a laboratory or medical professional. In some embodiments, the information or data includes a comparison of the level of at least one of the genes set forth in Table 1, 2, or 3 to a reference level. In some embodiments, the information or data includes an indication that at least one of the genes set forth in Table 1, 2, or 3 is present or absent in the sample. In some embodiments, the information or data includes an indication that the patient is suitably treated or not suitably treated with a therapy comprising a VEGF antagonist (e.g., an anti-VEGF antibody, e.g., bevacizumab).

The phrase "identifying a patient" or "identifies a patient" as used herein, refers to using the information or data generated relating to the level or presence of at least one of the genes set forth in Table 1, 2, or 3 in a sample of a patient to identify or selecting the patient as more likely to benefit or less likely to benefit from a therapy comprising a VEGF antagonist (e.g., an anti-VEGF antibody, e.g., bevacizumab). The information or data used or generated may be in any form, written, oral or electronic. In some embodiments, using the information or data generated includes communicating, presenting, reporting, storing, sending, transferring, supplying, transmitting, dispensing, or combinations thereof. In some embodiments, communicating, presenting, reporting, storing, sending, transferring, supplying, transmitting, dispensing, or combinations thereof are performed by a computing device, analyzer unit or combination thereof. In some further embodiments, communicating, presenting, reporting, storing, sending, transferring, supplying, transmitting, dispensing, or combinations thereof are performed by a laboratory or medical professional. In some embodiments, the information or data includes a comparison of the level of at least one of the genes set forth in Table 1, 2, or 3 to a reference level. In some embodiments, the information or data includes an indication that at least one of the genes set forth in Table 1, 2, or 3 is present or absent in the sample. In some embodiments, the information or data includes an indication that the patient is more likely or less likely to respond to a therapy comprising a VEGF antagonist (e.g., an anti-VEGF antibody, e.g., bevacizumab).

The phrase "selecting a therapy" or as used herein, refers to using the information or data generated relating to the level or presence of at least one of the genes set forth in Table 1, 2, or 3 in a sample of a patient to identify or selecting a therapy for a patient. In some embodiment the therapy may comprise a VEGF antagonist (e.g., an anti-VEGF antibody, e.g., bevacizumab). In some embodiments the phrase "selecting a therapy" includes the identification of a patient who requires adaptation of an effective amount of a VEGF antagonist (e.g., an anti-VEGF antibody, e.g., bevacizumab) being administered.

By "monotherapy" is meant a therapeutic regimen that includes only a single therapeutic agent for the treatment of the cancer or tumor during the course of the treatment period. Monotherapy using a VEGF antagonist (e.g., an anti-VEGF antibody, e.g., bevacizumab) means that the VEGF antagonist is administered in the absence of an additional anti-cancer therapy during treatment period.

The term "effective amount" refers to an amount of a drug effective to treat a disease or disorder, such as glioblastoma, in a subject or patient, such as a mammal, e.g., a human. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, duration of progression free survival (PFS), overall survival (OS), the response rates (RR), duration of response, and/or quality of life.

An "effective response" of a patient or a patient's "responsiveness" or "sensitivity" to treatment with a VEGF antagonist (e.g., an anti-VEGF antibody, e.g., bevacizumab) refers to the clinical or therapeutic benefit imparted to a patient at risk for or having a glioblastoma from or as a result of the treatment with the VEGF antagonist. Such benefit includes cellular or biological responses, a complete response, a partial response, a stable disease (without progression or relapse), or a response with a later relapse of the patient from or as a result of the treatment with the antagonist. For example, an effective response can be reduced tumor size, increased progression-free survival (PFS), and/or increased overall survival (OS) in a patient diagnosed as expressing a higher or lower level of one or more of the biomarkers set forth in Table 1, 2, or 3 compared to a reference level (including, e.g., the median expression level of the biomarker in a sample from a group/population of patients being tested for responsiveness to a VEGF antagonist; the median expression level of the biomarker in a sample from a group/population of patients having glioblastomas and identified as not responding to VEGF antagonist treatment; the level in a sample previously obtained from the individual at a prior time; or the level in a sample from a patient who received prior treatment with a VEGF antagonist (e.g., an anti-VEGF antibody, e.g., bevacizumab) in a primary tumor setting, and who now may be experiencing metastasis). The expression of genetic biomarker(s) effectively predicts, or predicts with high sensitivity, such effective response.

"Survival" refers to the subject remaining alive, and includes progression-free survival (PFS) and overall survival (OS). Survival can be estimated by the Kaplan-Meier method, and any differences in survival are computed using the stratified log-rank test.

"Overall survival" or "OS" refers to the subject remaining alive for a defined period of time, such as about 1 year, about 2 years, about 3 years, about 4 years, about 5 years, about 10 years, etc., from initiation of treatment or from initial diagnosis. In the studies underlying the present invention the event used for survival analysis was death from any cause.

"Progression-free survival" or "PFS" refers to the time from treatment (or randomization) to first disease progression or death. For example it is the time that the subject remains alive, without return of the cancer, e.g., for a defined period of time such as about 1 month, about 2 months, about 3 months, about 4, months, about 5 months, about 6 months, about 7 months, about 8 months, about 9 months, about 1 year, about 2 years, about 3 years, etc., from initiation of treatment or from initial diagnosis. In one aspect of the invention, PFS can be assessed by the MacDonald Response Criteria as described in MacDonald et al. (*J. Clin. Oncol.* 1990; 8: 1277-80, 1990).

"Overall response rate" or "Objective response rate" (ORR) refers to the percentage of people who experience a decrease in the size or amount of the cancer (e.g., the glioblastoma) for a minimum amount of time, and ORR can be represented by the sum of the complete and partial response rates.

By "extending survival" or "increasing the likelihood of survival" is meant increasing PFS and/or OS in a treated subject (e.g., a subject treated with a VEGF antagonist (e.g., an anti-VEGF antibody, e.g., bevacizumab)) or population of treated subjects relative to an untreated subject (e.g., a subject not treated with a VEGF antibody) or population of untreated subjects, respectively, or relative to a control treatment protocol, such as treatment only with the chemotherapeutic agent, such as those uses in the standard of care for glioblastoma, such as, for example, temozolomide (TMZ) with or without radiotherapy. Survival is monitored for at least about one month, about two months, about four months, about six months, about nine months, or at least about 1 year, or at least about 2 years, or at least about 3 years, or at least about 4 years, or at least about 5 years, or at least about 10 years, etc., following the initiation of treatment or following the initial diagnosis.

Hazard ratio (HR) is a statistical definition for rates of events. For the purpose of the invention, hazard ratio is defined as representing the probability of an event in the experimental arm divided by the probability of an event in the control arm at any specific point in time. "Hazard ratio" in progression free survival analysis is a summary of the difference between two progression free survival curves, representing the reduction in the risk of death on treatment compared to control, over a period of follow-up.

A "patient" or "subject" herein refers to any single animal (including, for example, a mammal, such as a dog, a cat, a horse, a rabbit, a zoo animal, a cow, a pig, a sheep, a non-human primate, and a human), such as a human, eligible for treatment who is experiencing or has experienced one or more signs, symptoms, or other indicators of a disease or disorder, such as a glioblastoma (GBM). Intended to be included as a patient are any patients involved in clinical research trials not showing any clinical sign of disease, or patients involved in epidemiological studies, or patients once used as controls. The patient may have been previously treated with a VEGF antagonist (e.g., an anti-VEGF antibody, e.g., bevacizumab) or another drug, or not so treated. The patient may be naïve to an additional drug(s) being used when the treatment herein is started, i.e., the patient may not have been previously treated with, for example, a therapy other than a VEGF antagonist (e.g., an anti-VEGF antibody, e.g., bevacizumab) at "baseline" (i.e., at a set point in time before the administration of a first dose of a VEGF antagonist (e.g., an anti-VEGF antibody, e.g., bevacizumab) in the treatment method herein, such as the day of screening the subject before treatment is commenced). Such "naïve" patients or subjects are generally considered to be candidates for treatment with such additional drug(s).

The terms "cancer" and "cancerous" refer to or describe the physiological condition in mammals that is typically characterized by unregulated cell growth. Included in this definition are benign and malignant cancers as well as dormant tumors or micrometastatses. Examples of cancer include but are not limited to, carcinoma, lymphoma, blastoma, sarcoma, and leukemia. More particular examples of such cancers include, but are not limited to, glioblastoma (GBM), including, e.g., proneural GBM, neural GBM, classical GBM, and mesenchymal GBM. GBM may be newly diagnosed, diagnosed, or recurrent. Other cancers include, for example, breast cancer, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, ovarian cancer, cervical cancer, liver cancer, bladder cancer, hepatoma, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder," and "tumor" are not mutually exclusive as referred to herein.

The term "pharmaceutical formulation" refers to a sterile preparation that is in such form as to permit the biological activity of the medicament to be effective, and which contains no additional components that are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

A "kit" is any manufacture (e.g., a package or container) comprising at least one reagent, e.g., a medicament for treatment of a patient having a glioblastoma or a probe for specifically detecting a biomarker gene or protein of the invention. The manufacture is preferably promoted, distributed, or sold as a unit for performing the methods of the present invention.

As used herein, the term "covariate" refers to certain variables or information relating to a patient. The clinical endpoints are frequently considered in regression models, where the endpoints represent the dependent variable and the biomarkers represent the main or target independent variables (regressors). If additional variables from the clinical data pool are considered, they are denoted as (clinical) covariates.

The term "clinical covariate" is used herein to describe all clinical information about the patient, which is in general available at baseline. These clinical covariates comprise demographic information like sex, age, etc., other anamnestic information, concomitant diseases, concomitant therapies, results of physical examinations, common laboratory parameters obtained, known properties of the angiogenic disorders, clinical disease staging, timing and result of pretreatments, disease history, as well as all similar information that may be associated with the clinical response to treatment.

As used herein, the term "raw analysis" or "unadjusted analysis" refers to regression analyses, wherein besides the considered biomarkers, no additional clinical covariates are used in the regression model, neither as independent factors nor as stratifying covariate.

As used herein, the term "adjusted by covariates" refers to regression analyses, wherein besides the considered biomarkers, additional clinical covariates are used in the regression model, either as independent factors or as stratifying covariate.

As used herein, the term "univariate" refers to regression models or graphical approaches wherein, as an independent variable, only one of the target biomarkers is part of the model. These univariate models can be considered with and without additional clinical covariates.

As used herein, the term "multivariate" refers to regression models or graphical approaches wherein, as independent variables, more than one of the target biomarkers is part of the model. These multivariate models can be considered with and without additional clinical covariates.

III. Methods to Identify Patients Responsive to VEGF Antagonists

The present invention provides methods for identifying and/or monitoring patients likely to be responsive to VEGF antagonist (e.g., anti-VEGF antibody, e.g., bevacizumab) therapy. The methods are useful, inter alia, for increasing the likelihood that administration of a VEGF antagonist (e.g., an anti-VEGF antibody, e.g., bevacizumab) to a patient will be efficacious. The methods comprise detecting expression of one or more genetic biomarkers in a biological sample from a patient, wherein the expression of one or more such biomarkers is indicative of whether the patient is sensitive or responsive to VEGF antagonists, such as anti-VEGF antibodies.

More particularly, determining the expression level of at least one of the genes set forth in Table 1, 2, or 3 below (e.g., 1, 2, 3, 4, 5, 6, 7, 8, 9, or 10 of the genes listed in Table 3 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, or 60 or more different genes) listed in Table 2 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100 or more different genes) listed in Table 1) in a sample from a patient is useful for monitoring whether the patient is responsive or sensitive to a VEGF antagonist, such as an anti-VEGF antibody. For any of the methods described herein, one could, for example, determine the expression levels of any combination of 2, 3, 4, 5, 6, 7, 8, 9, or 10 genes selected from the genes listed in Table 3. Alternatively, for any of the methods described herein, the expression level of all 10 genes (NCAM1, OMG, PRKCZ, GALNT13, GPR17, DNM3, FERMT1, SNAP91, ABHD6, and PFN2) listed in Table 3 can be determined.

TABLE 1

108 genes from Phillips' extended classifier gene list represented on the Nanostring platform

| | | | | |
|---|---|---|---|---|
| ABHD6 | COL4A2 | GALNT13 | PI3 | TMEM100 |
| ACTN1 | CRYAB | GGH | PKNOX2 | TNC |
| ANGPT2 | CSDC2 | GGTA1P | PLA2G5 | TOP2A |
| ANGPTL4 | CSMD3 | GINS1 | PRKCZ | TRMT6 |
| AP2B1 | DBF4 | GINS2 | PTGDS | TTK |
| ASCL1 | DEF6 | GRIA2 | RASL10A | TYMS |
| ATP6V1G2 | DHFR | HMMR | RBM24 | FLT1 |
| BCAN | DLL1 | HEY2 | RHOJ | ZNF367 |
| BCL3 | DLL3 | ICAM1 | RTN1 | |
| BMP2 | DNAJC12 | KIAA0101 | RYR3 | |
| BRIP1 | DNM3 | KLRC3 | S100A11 | |
| RGCC | DPP10 | LIF | SCD | |
| CA12 | DTL | MELK | SCG3 | |
| CCNB1 | E2F7 | MYL9 | SERPINA1 | |
| CCNE2 | ECT2 | NCAM1 | SERPINE1 | |
| CD274 | EFNB2 | NDRG2 | SERPINH1 | |
| CDC6 | EMP3 | NRP1 | SMC4 | |
| CDCA7 | ESM1 | NRP2 | SNAP91 | |
| CDKN2A | EXOSC9 | OLIG2 | SOX8 | |
| CDKN2C | EZH2 | OMG | SPOCD1 | |
| CENPK | FAM20C | PCNA | KIAA1244 | |
| CHEK1 | FANCI | PDGFA | STEAP3 | |
| CHI3L1 | FERMT1 | PDK1 | SUSD5 | |
| CNTN3 | FOSL2 | PDLIM4 | TAGLN | |
| COL4A1 | GABBR1 | PDPN | TIMP1 | |

TABLE 2

65 shrunken-centroid subtype classifier genes

| | | | | |
|---|---|---|---|---|
| NCAM1 | KLRC3 | CSDC2 | SUSD5 | COL6A3 |
| OMG | DLL1 | BEX1 | PTX3 | LUM |
| PRKCZ | BCAS1 | POSTN | CNTN3 | CHI3L1 |
| GALNT13 | SOX8 | S100A4 | LIF | C8orf4 |
| GPR17 | TMEFF2 | ZBTB18 | BCL3 | SERPINE1 |
| DNM3 | SERPINH1 | EPHB4 | PRF1 | SCG3 |
| FERMT1 | GRIA2 | OLIG2 | SYT4 | TXNDC5 |
| SNAP91 | AKT3 | CSMD3 | GABBR1 | PTPRO |
| ABHD6 | LGALS3 | MAP2 | PHLPP1 | MXD4 |
| PFN2 | TIMP1 | ASCL1 | EFNB2 | PROM1 |
| KIAA1244 | DPP10 | CTNND2 | KCND2 | NDRG2 |
| ATP6V1G2 | ERBB4 | NDRG4 | FBLIM1 | DDX25 |
| ERBB3 | DLL3 | EMP3 | FAM20C | BCAN |

TABLE 3

10 exemplary classifier genes

NCAM1
OMG
PRKCZ
GALNT13

TABLE 3-continued 10 exemplary classifier genes

GPR17
DNM3
FERMT1
SNAP91
ABHD6
PFN2

In one example, determining the expression level of at least 1, 2, 3, 4, 5, 6, 7, 8, 9, or 10 of the genes listed in Table 3 and at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, or 60 or more different genes) listed in Table 2 in a sample from a patient is useful for monitoring whether the patient is responsive or sensitive to a VEGF antagonist, such as an anti-VEGF antibody, such as bevacizumab. In one example, determining the expression level of at least 1, 2, 3, 4, 5, 6, 7, 8, 9, or 10 of the genes listed in Table 3 and at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100 or more different genes) listed in Table 1 in a sample from a patient is useful for monitoring whether the patient is responsive or sensitive to a VEGF antagonist, such as an anti-VEGF antibody, such as bevacizumab. In one example, determining the expression level of all 108 genes listed in Table 1 in a sample from a patient is useful for monitoring whether the patient is responsive or sensitive to a VEGF antagonist, such as an anti-VEGF antibody, such as bevacizumab.

In some instances, for any of the methods described herein, the expression level of at least 10 genes (e.g., 10, 20, 25, 30, 35, 40, 45, 50 or more genes) in total can be determined. In other instances, for any of the methods described herein, the expression level of 65 or more genes (e.g., 65, 70, 75, 80, 85, 90, 95, 100, or 105 or more genes) in total can be determined.

The disclosed methods and assays provide for convenient, efficient, and potentially cost-effective means to obtain data and information useful in assessing appropriate or effective therapies for treating patients. For example, a patient can provide a tissue sample (e.g., a tumor biopsy or a blood sample) before and/or after treatment with a VEGF antagonist and the sample can be examined by way of various in vitro assays to determine whether the patient's cells are sensitive to a VEGF antagonist, such as an anti-VEGF antibody, such as bevacizumab.

The invention also provides methods for monitoring the sensitivity or responsiveness of a patient to a VEGF antagonist (e.g., an anti-VEGF antibody, e.g., bevacizumab). The methods may be conducted in a variety of assay formats, including assays detecting genetic or protein expression (such as PCR and enzyme immunoassays) and biochemical assays detecting appropriate activity. Determination of expression or the presence of such biomarkers in patient samples is predictive of whether a patient is sensitive to the biological effects of a VEGF antagonist, such as an anti-VEGF antibody, such as bevacizumab. Applicants' invention herein is that a difference or change (i.e., an increase or decrease) in the expression of the 1, 2, 3, 4, 5, 6, 7, 8, 9, or 10 of the genes listed in Table 3 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, or 60 or more different genes) listed in Table 2 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100 or more different genes) listed in Table 1 in a sample from a patient having a glioblastoma relative to a reference level (including, e.g., the median expression level of the biomarker in a sample from a group/population of patients being tested for responsiveness to a VEGF antagonist or the median expression level of the biomarker in a sample from a group/population of patients having glioblastomas and identified as not responding to VEGF antagonist treatment) correlates with treatment of such a patient with a VEGF antagonist, such as an anti-VEGF antibody, such as bevacizumab.

Example 5 shows that increased expression levels of at least one of NCAM1, OMG, PRKCZ, GALNT13, GPR17, DNM3, FERMT1, SNAP91, ABHD6, and PFN2 (e.g., 1, 2, 3, 4, 5, 6, 7, 8, 9, or 10 of the genes) relative to reference levels of the at least one evaluated biomarker identifies a patient who is likely to respond to treatment with a VEGF antagonist, such as an anti-VEGF antibody, such as bevacizumab. Optionally, expression levels of at least one of NCAM1, OMG, PRKCZ, GALNT13, GPR17, DNM3, FERMT1, SNAP91, ABHD6, and PFN2 (e.g., 1, 2, 3, 4, 5, 6, 7, 8, 9, or 10 of the genes) determined in combination with one or more genes set forth in Table 1, 2, or 3, relative to reference levels of the at least one evaluated biomarker, can also be useful for identifying a patient who is likely to respond to treatment with a VEGF antagonist, such as an anti-VEGF antibody, such as bevacizumab. Typically, a difference or a change (i.e., a decrease or increase) of at least about 1.5-fold, 1.6-fold, 1.8-fold, 2-fold, 3-fold, 4-fold, 5-fold, 6-fold, 7-fold, 8-fold, 9-fold, or 10-fold in expression in at least one of the genes relative to reference levels (e.g., the median expression level(s) of the biomarker(s) in a sample from a group/population of patients having glioblastomas and being tested for responsiveness to a VEGF antagonist or the median expression level(s) of the biomarker(s) in a sample from a group/population of patients having glioblastomas and identified as not responding to VEGF antagonist treatment) or a difference or a change (i.e., a decrease or increase) of an average log ratio of at least about −2, −3, −4, −5, or −6 standard deviations from the mean expression level(s) of the gene(s) measured indicates that a patient will respond to or be sensitive to treatment with a VEGF antagonist.

According to the methods of the invention, the likelihood that a particular individual (e.g., a patient) is likely to respond to treatment with a VEGF antagonist can be determined by detecting the expression level of at least one of the genes listed in Table 1, 2, or 3 (e.g., 1, 2, 3, 4, 5, 6, 7, 8, 9, or 10 of the genes listed in Table 3 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, or 60 or more different genes) listed in Table 2 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100 or more different genes) listed in Table 1) and comparing the expression level of the gene to a reference expression level. For example, as noted above, the reference expression level may be the median expression level of the at least one gene in a group/population of patients having glioblastomas and being tested for responsiveness to a VEGF antagonist (e.g., an anti-VEGF antibody, e.g., bevacizumab). In some embodiments, the reference expression level is the median level of expression of the at least one gene in patients having glioblastomas and identified as not responding to VEGF antagonist (e.g., an anti-VEGF antibody, e.g., bevacizumab) treatment. In some embodiments, the reference expression level is the expression level of the at least one gene in a sample previously obtained from the individual at a prior time. In other embodiments, the individuals are patients who received prior treatment with a VEGF antagonist in a primary tumor setting. In some embodiments, the individuals are patients who are experiencing metastasis. Individuals who have an expression level that is greater than or less than the reference expression level of at least one biomarker gene as described herein are identified as subjects/patients likely to respond to treatment with a VEGF antagonist. Subjects/patients who exhibit gene expression levels at, for example, 50%, 45%, 40%, 35%, 30%, 25%, 20%, 15%, 10%, or 5% relative to (i.e., higher or lower than) the median are identified as patients likely to respond to treatment with a VEGF antagonist (e.g., an anti-VEGF antibody, e.g., bevacizumab). The subjects/patients may be informed that they have an increased likelihood of being responsive to treatment with a VEGF antagonist and/or provided a recommendation that anti-cancer therapy include a VEGF antagonist. The gene expression level can be determined using at least one of the biomarker genes as described herein, or any linear combination of the biomarker genes as described herein (e.g., mean, weighted mean, or median) using methods known in the art and described in, e.g., Sokal R. R. and Rholf, F. J. (1995) "Biometry: the principles and practice of statistics in biological research," W.H. Freeman and Co. New York, N.Y.

In one aspect, this invention provides a method of determining whether a patient having a glioblastoma will respond to treatment with a VEGF antagonist, such as an anti-VEGF antibody (e.g., bevacizumab), comprising assessing, as a biomarker, expression of at least one of the genes listed in Table 1, 2, or 3 (e.g., 1, 2, 3, 4, 5, 6, 7, 8, 9, or 10 of the genes listed in Table 3 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, or 60 or more different genes) listed in Table 2 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100 or more different genes) listed in Table 1) in a sample from the patient obtained either (i) before any VEGF antagonist has been administered to the patient, or (ii) before and after such treatment. A change (i.e., increase or decrease) in the expression of the at least one of the genes relative to a reference level (see above) indicates that the patient will likely respond to treatment with a VEGF antagonist, such as an anti-VEGF antibody (e.g., bevacizumab). The patient may be informed that they have an increased likelihood of responding to treatment with a VEGF antagonist and/or provided a recommendation that anti-cancer therapy include a VEGF antagonist.

In another aspect, the invention provides a method of optimizing therapeutic efficacy of an anti-cancer therapy for a patient having a glioblastoma, comprising detecting, as a biomarker, expression of at least one of the genes listed in Table 1, 2, or 3 (e.g., 1, 2, 3, 4, 5, 6, 7, 8, 9, or 10 of the genes listed in Table 3 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, or 60 or more different genes) listed in Table 2 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100 or more different genes) listed in Table 1) in a sample from the patient obtained either (i) before any VEGF antagonist has been administered to the patient, or (ii) before and after such treatment. A change (i.e., increase or decrease) in the expression of the at least one of the genes relative to a reference level (see above) indicates that the patient will likely respond to treatment with a VEGF antagonist, such as an anti-VEGF antibody (e.g., bevacizumab). The patient may be informed that they have an increased likelihood of responding to treatment with a VEGF antagonist and/or provided a recommendation that anti-cancer therapy include a VEGF antagonist.

In another aspect, the invention provides a method for selecting a therapy for a patient having a glioblastoma, comprising detecting, as a biomarker, expression of at least one of the genes listed in Table 1, 2, or 3 (e.g., 1, 2, 3, 4, 5, 6, 7, 8, 9, or 10 of the genes listed in Table 3 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, or 60 or more different genes) listed in Table 2 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100 or more different genes) listed in Table 1) in a sample from the patient obtained either (i) before any VEGF antagonist has been administered to the patient, or (ii) before and after such treatment. A change (i.e., increase or decrease) in the expression of the at least one of the genes relative to a reference level (see above) indicates that the patient will likely respond to treatment with a VEGF antagonist, such as an anti-VEGF antibody (e.g., bevacizumab). A therapy including VEGF antagonist (e.g., an anti-VEGF antibody, e.g., bevacizumab) may be selected if the patient is identified as likely to respond to treatment with a VEGF antagonist, and the patient may be provided a recommendation of the selected therapy including the VEGF antagonist.

In another embodiment, the present invention provides a method of monitoring the sensitivity or responsiveness of a patient to a VEGF antagonist, such as an anti-VEGF antibody. This method comprises assessing gene expression of at least one of the genes listed in Table 1, 2, or 3 (e.g., 1, 2, 3, 4, 5, 6, 7, 8, 9, or 10 of the genes listed in Table 3 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, or 60 or more different genes) listed in Table 2 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100 or more different genes) listed in Table 1) from a patient sample and predicting the sensitivity or responsiveness of the patient to the VEGF antagonist, such as an anti-VEGF antibody (e.g., bevacizumab), wherein a change (i.e., increase or decrease) in the expression of at least one gene listed in Table 1, 2, or 3 correlates with sensitivity or responsiveness of the patient to effective treatment with the VEGF antagonist. According to one embodiment of this method, a biological sample is obtained from the patient before administration of any VEGF antagonist and subjected to an assay to evaluate the level of expression products of at least one gene in the sample. If expression of at least one of the genes listed in Table 1, 2, or 3 is changed (i.e., increased or decreased) relative to a reference level (e.g., see above), the patient is determined to be sensitive or responsive to treatment with a VEGF antagonist, such as an anti-VEGF antibody. The patient may be informed that they have an increased likelihood of being sensitive or responsive to treatment with a VEGF antagonist and/or provided a recommendation that anti-cancer therapy include a VEGF antagonist. In another embodiment of this method, a biological sample is obtained from the patient before and after administration of a VEGF antagonist, as described herein.

Those of skill in the medical arts, particularly pertaining to the application of diagnostic tests and treatment with therapeutics, will recognize that biological systems are somewhat variable and not always entirely predictable, and thus many good diagnostic tests or therapeutics are occasionally ineffective. Thus, it is ultimately up to the judgment of the attending physician to determine the most appropriate course of treatment for an individual patient, based upon test results, patient condition and history, and his or her own experience. There may even be occasions, for example, when a physician will choose to treat a patient with a VEGF antagonist, such as an anti-VEGF antibody (e.g., bevacizumab), even when a patient is not predicted to be particularly sensitive to VEGF antagonists, based on data from diagnostic tests or from other criteria, particularly if all or most of the other obvious treatment options have failed, or if some synergy is anticipated when given with another treatment.

In further expressed embodiments, the present invention provides a method of predicting the sensitivity of a patient to treatment with a VEGF antagonist, such as an anti-VEGF antibody (e.g., bevacizumab), or predicting whether a patient will respond effectively to treatment with a VEGF antagonist, comprising assessing the level of one or more of the genetic biomarkers identified herein expressed in the sample; and predicting the sensitivity of the patient to inhibition by a VEGF antagonist, wherein expression levels of one or more of these genetic biomarkers correlates with high sensitivity of the patient to effective response to treatment with a VEGF antagonist.

The sample may be taken from a patient who is suspected of having, or is diagnosed as having a glioblastoma, and hence is likely in need of treatment, or from a normal individual who is not suspected of having any disorder. For assessment of marker expression, patient samples, such as those containing cells, or proteins or nucleic acids produced by these cells, may be used in the methods of the present invention. In the methods of this invention, the level of a biomarker can be determined by assessing the amount (e.g., the absolute amount or concentration) of the markers in a sample, preferably a tissue sample (e.g., a tumor tissue sample, such as a biopsy). In addition, the level of a biomarker can be assessed in bodily fluids or excretions containing detectable levels of biomarkers. Bodily fluids or secretions useful as samples in the present invention include, e.g., blood, urine, saliva, stool, pleural fluid, lymphatic fluid, sputum, ascites, prostatic fluid, cerebrospinal fluid (CSF), or any other bodily secretion or derivative thereof. The word "blood" is meant to include whole blood, plasma, serum, or any derivative of blood. Assessment of a biomarker in such bodily fluids or excretions can sometimes be preferred in circumstances where an invasive sampling method is inappropriate or inconvenient. However, in the case of samples that are bodily fluids, the sample to be tested herein is preferably blood, synovial tissue, or synovial fluid, most preferably blood.

The sample may be frozen, fresh, fixed (e.g., formalin fixed), centrifuged, and/or embedded (e.g., paraffin embedded), etc. The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the marker in the sample. Likewise, biopsies may also be subjected to post-collection preparative and storage techniques, e.g., fixation.

In any of the methods described herein, the individual (e.g., patient/subject) may be informed of an increased or decreased likelihood of being sensitive or responsive to treatment with a VEGF antagonist (e.g., an anti-VEGF antibody, e.g., bevacizumab); provided a recommendation of an anti-cancer therapy (e.g., an anti-cancer therapy that includes or does not include a VEGF antagonist); and/or selected a suitable therapy (e.g., a VEGF antagonist and/or other anti-angiogenic agent).

A. Detection of Gene Expression

The genetic biomarkers described herein can be detected using any method known in the art. For example, tissue or cell samples from mammals can be conveniently assayed for, e.g., mRNAs or DNAs from a genetic biomarker of interest using Northern, dot-blot, or polymerase chain reaction (PCR) analysis, array hybridization, RNase protection assay, or using DNA SNP chip microarrays, which are commercially available, including DNA microarray snapshots. For example, real-time PCR (RT-PCR) assays such as quantitative PCR assays are well known in the art. In an illustrative embodiment of the invention, a method for detecting mRNA from a genetic biomarker of interest in a biological sample, such as a tumor sample (e.g., a glioblastoma tumor sample), comprises producing cDNA from the sample by reverse transcription using at least one primer; amplifying the cDNA so produced; and detecting the presence of the amplified cDNA. In addition, such methods can include one or more steps that allow one to determine the levels of mRNA in a biological sample (e.g., by simultaneously examining the levels a comparative control mRNA sequence of a "housekeeping" gene such as an actin family member). Optionally, the sequence of the amplified cDNA can be determined.

1. Detection of Nucleic Acids

In one specific embodiment, expression of the biomarker genes as described herein can be performed by RT-PCR technology. Probes used for PCR may be labeled with a detectable marker, such as, for example, a radioisotope, fluorescent compound, bioluminescent compound, a chemiluminescent compound, metal chelator, or enzyme. Such probes and primers can be used to detect the presence of expressed genes set forth in Table 1, 2, or 3 in a sample. As will be understood by the skilled artisan, a great many different primers and probes may be prepared and used effectively to amplify, clone and/or determine the presence and/or levels expressed of one or more of the genes listed in Table 1, 2, and 3.

Other methods include protocols that examine or detect mRNAs from at least one of the genes listed in Table 1, 2, or 3 (e.g., 1, 2, 3, 4, 5, 6, 7, 8, 9, or 10 of the genes listed in Table 3 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, or 60 or more different genes) listed in Table 2 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100 or more different genes) listed in Table 1) in a tissue (e.g., a tumor tissue, e.g., a glioblastoma tumor tissue) or cell sample by microarray technologies. Using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes that have potential to be expressed in certain disease states may be arrayed on a solid support. Hybridization of a labeled probe with a particular array member indicates that the sample from which the probe was derived expresses that gene. Differential gene expression analysis of disease tissue can provide valuable information. Microarray technology utilizes nucleic acid hybridization techniques and computing technology to evaluate the mRNA expression profile of thousands of genes within a single experiment (see, e.g., WO 2001/75166). See, for example, U.S. Pat. Nos. 5,700,637, 5,445,934, and 5,807,522, Lockart, *Nature Biotechnology* 14:1675-1680 (1996); and Cheung et al., *Nature Genetics* 21(Suppl):15-19 (1999) for a discussion of array fabrication.

In addition, the DNA profiling and detection method utilizing microarrays described in EP 1753878 may be employed. This method rapidly identifies and distinguishes between different DNA sequences utilizing short tandem repeat (STR) analysis and DNA microarrays. In an embodiment, a labeled STR target sequence is hybridized to a DNA microarray carrying complementary probes. These probes vary in length to cover the range of possible STRs. The labeled single-stranded regions of the DNA hybrids are selectively removed from the microarray surface utilizing a post-hybridization enzymatic digestion. The number of repeats in the unknown target is deduced based on the pattern of target DNA that remains hybridized to the microarray.

One example of a microarray processor is the Affymetrix GENECHIP® system, which is commercially available and comprises arrays fabricated by direct synthesis of oligonucleotides on a glass surface. Other systems may be used as known to one skilled in the art.

Other methods for determining the level of the biomarker besides RT-PCR or another PCR-based method include proteomics techniques, as well as individualized genetic profiles that are necessary to treat angiogenic disorders based on patient response at a molecular level. The specialized microarrays herein, e.g., oligonucleotide microarrays or cDNA microarrays, may comprise one or more biomarkers having expression profiles that correlate with either sensitivity or resistance to one or more anti-VEGF antibodies. Other methods that can be used to detect nucleic acids, for use in the invention, involve high throughput RNA sequence expression analysis, including RNA-based genomic analysis, such as, for example, RNASeq.

Many references are available to provide guidance in applying the above techniques (Kohler et al., *Hybridoma Techniques* (Cold Spring Harbor Laboratory, New York, 1980); Tijssen, *Practice and Theory of Enzyme Immunoassays* (Elsevier, Amsterdam, 1985); Campbell, *Monoclonal Antibody Technology* (Elsevier, Amsterdam, 1984); Hurrell, *Monoclonal Hybridoma Antibodies: Techniques and Applications* (CRC Press, Boca Raton, Fla., 1982); and Zola, *Monoclonal Antibodies: A Manual of Techniques*, pp. 147-158 (CRC Press, Inc., 1987)). Northern blot analysis is a conventional technique well known in the art and is described, for example, in *Molecular Cloning, a Laboratory Manual*, second edition, 1989, Sambrook, Fritch, Maniatis, Cold Spring Harbor Press, 10 Skyline Drive, Plainview, N.Y. 11803-2500. Typical protocols for evaluating the status of genes and gene products are found, for example in Ausubel et al., eds., 1995, *Current Protocols In Molecular Biology*, Units 2 (Northern Blotting), 4 (Southern Blotting), 15 (Immunoblotting) and 18 (PCR Analysis).

2. Detection of Proteins

As to detection of protein biomarkers such as a protein biomarker corresponding to at least one of the genes listed in Table 1, 2, or 3 (e.g., 1, 2, 3, 4, 5, 6, 7, 8, 9, or 10 of the genes listed in Table 3 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, or 60 or more different genes) listed in Table 2 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100 or more different genes) listed in Table 1), for example, various protein assays are available including, for example, antibody-based methods as well as mass spectroscopy and other similar means known in the art. In the case of antibody-based methods, for example, the sample may be contacted with an antibody specific for said biomarker under conditions sufficient for an antibody-biomarker complex to form, and then detecting said complex. Detection of the presence of the protein biomarker may be accomplished in a number of ways, such as by Western blotting (with or without immunoprecipitation), 2-dimensional SDS-PAGE, immunoprecipitation, fluorescence activated cell sorting (FACS), flow cytometry, and ELISA procedures for assaying a wide variety of tissues and samples, including plasma or serum. A wide range of immunoassay techniques using such an assay format are available, see, e.g., U.S. Pat. Nos. 4,016,043, 4,424,279, and 4,018,653. These include both single-site and two-site or "sandwich" assays of the non-competitive types, as well as in the traditional competitive binding assays. These assays also include direct binding of a labeled antibody to a target biomarker.

Sandwich assays are among the most useful and commonly used assays. A number of variations of the sandwich assay technique exist, and all are intended to be encompassed by the present invention. Briefly, in a typical forward assay, an unlabelled antibody is immobilized on a solid substrate, and the sample to be tested brought into contact with the bound molecule. After a suitable period of incubation, for a period of time sufficient to allow formation of an antibody-antigen complex, a second antibody specific to the antigen, labeled with a reporter molecule capable of producing a detectable signal is then added and incubated, allowing time sufficient for the formation of another complex of antibody-antigen-labeled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of biomarker.

Variations on the forward assay include a simultaneous assay, in which both sample and labeled antibody are added simultaneously to the bound antibody. These techniques are well known to those skilled in the art, including any minor variations as will be readily apparent. In a typical forward sandwich assay, a first antibody having specificity for the biomarker is either covalently or passively bound to a solid surface. The solid surface is typically glass or a polymer, the most commonly used polymers being cellulose, polyacrylamide, nylon, polystyrene, polyvinyl chloride, or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g., 2-40 minutes or overnight if more convenient) and under suitable conditions (e.g., from room temperature to 40° C. such as between 25° C. and 32° C. inclusive) to allow binding of any subunit present in the antibody. Following the incubation period, the antibody subunit solid phase is washed and dried and incubated with a second antibody specific for a portion of the biomarker. The second antibody is linked to a reporter molecule which is used to indicate the binding of the second antibody to the molecular marker.

An alternative method involves immobilizing the target biomarkers in the sample and then exposing the immobilized target to specific antibody which may or may not be labeled with a reporter molecule. Depending on the amount of target and the strength of the reporter molecule signal, a bound target may be detectable by direct labeling with the antibody. Alternatively, a second labeled antibody, specific to the first antibody is exposed to the target-first antibody complex to form a target-first antibody-second antibody tertiary complex. The complex is detected by the signal emitted by the reporter molecule. By "reporter molecule," as used in the present specification, is meant a molecule which, by its chemical nature, provides an analytically identifiable signal which allows the detection of antigen-bound antibody. The most commonly used reporter molecules in this type of assay are either enzymes, fluorophores or radionuclide containing molecules (i.e., radioisotopes) and chemiluminescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase, and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labeled antibody is added to the first antibody-molecular marker complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of biomarker which was present in the sample. Alternately, fluorescent compounds, such as fluorescein and rhodamine, may be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic color visually detectable with a light microscope. As in the EIA, the fluorescent labeled antibody is allowed to bind to the first antibody-molecular marker complex. After washing off the unbound reagent, the remaining tertiary complex is then exposed to the light of the appropriate wavelength, the fluorescence observed indicates the presence of the molecular marker of interest. Immunofluorescence and EIA techniques are both very well established in the art. However, other reporter molecules, such as radioisotope, chemiluminescent or bioluminescent molecules, may also be employed.

B. Kits

For use in detection of the biomarkers, kits or articles of manufacture are also provided by the invention. Such kits can be used to determine whether a patient may benefit from treatment with a VEGF antagonist (e.g., an anti-VEGF antibody, e.g., bevacizumab). These kits may comprise polypeptides or polynucleotides capable of determining the expression level of at least one of the genes listed in Table 1, 2, or 3 (e.g., 1, 2, 3, 4, 5, 6, 7, 8, 9, or 10 of the genes listed in Table 3 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, or 60 or more different genes) listed in Table 2 and/or at least one different gene (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100 or more different genes) listed in Table 1) and instructions for use of the polypeptides or polynucleotides to determine the expression level of at least one of the genes set forth in Table 1, 2, or 3. If expression of at least one of the genes listed in Table 1, 2, or 3 is changed (i.e., increased or decreased) relative to or different from a reference level (e.g., see above), the patient may benefit from treatment with a VEGF antagonist, such as an anti-VEGF antibody (e.g., bevacizumab). The patient may be subsequently informed that they have an increased likelihood of being sensitive or responsive to treatment with a VEGF antagonist and/or provided a recommendation that anti-cancer therapy include a VEGF antagonist.

These kits may comprise a carrier means being compartmentalized to receive in close confinement one or more container means such as vials, tubes, and the like, each of the container means comprising one of the separate compounds or elements to be used in the method. For example, one of the container means may comprise a probe that is or can be detectably labeled. Such probe may be a polypeptide (e.g., an antibody) or polynucleotide specific for a protein or message, respectively. Where the kit utilizes nucleic acid hybridization to detect the target nucleic acid, the kit may also have containers containing nucleotide(s) for amplification of the target nucleic acid sequence and/or a container comprising a reporter-means, such as a biotin-binding protein, e.g., avidin or streptavidin, bound to a reporter molecule, such as an enzymatic, florescent, or radioisotope label.

Such kit will typically comprise the container described above and one or more other containers comprising materials desirable from a commercial and user standpoint, including buffers, diluents, filters, needles, syringes, and package inserts with instructions for use. A label may be present on the container to indicate that the composition is used for a specific application, and may also indicate directions for either in vivo or in vitro use, such as those described above.

The kits of the invention have a number of embodiments. A typical embodiment is a kit comprising a container, a label on said container, and a composition contained within said container, wherein the composition includes a primary antibody that binds to a protein or autoantibody biomarker, and the label on said container indicates that the composition can be used to evaluate the presence of such proteins or antibodies in a sample, and wherein the kit includes instructions for using the antibody for evaluating the presence of biomarker proteins in a particular sample type. The kit can further comprise a set of instructions and materials for preparing a sample and applying antibody to the sample. The kit may include both a primary and secondary antibody, wherein the secondary antibody is conjugated to a label, e.g., an enzymatic label.

Another embodiment is a kit comprising a container, a label on said container, and a composition contained within said container, wherein the composition includes one or more polynucleotides that hybridize to a complement of a biomarker as described herein under stringent conditions, and the label on said container indicates that the composition can be used to evaluate the presence of a biomarker as described herein in a sample, and wherein the kit includes instructions for using the polynucleotide(s) for evaluating the presence of the biomarker RNA or DNA in a particular sample type.

Other optional components of the kit include one or more buffers (e.g., block buffer, wash buffer, substrate buffer, etc.), other reagents such as substrate (e.g., chromogen) that is chemically altered by an enzymatic label, epitope retrieval solution, control samples (positive and/or negative controls), control slide(s), etc. Kits can also include instructions for interpreting the results obtained using the kit.

In further specific embodiments, for antibody-based kits, the kit can comprise, for example: (1) a first antibody (e.g., attached to a solid support) that binds to a biomarker protein; and, optionally, (2) a second, different antibody that binds to either the protein or the first antibody and is conjugated to a detectable label.

For oligonucleotide-based kits, the kit can comprise, for example: (1) an oligonucleotide, e.g., a detectably labeled oligonucleotide, which hybridizes to a nucleic acid sequence encoding a biomarker protein or (2) a pair of primers useful for amplifying a biomarker nucleic acid molecule. The kit can also comprise, e.g., a buffering agent, a preservative, or a protein stabilizing agent. The kit can further comprise components necessary for detecting the detectable label (e.g., an enzyme or a substrate). The kit can also contain a control sample or a series of control samples that can be assayed and compared to the test sample. Each component of the kit can be enclosed within an individual container and all of the various containers can be within a single package, along with instructions for interpreting the results of the assays performed using the kit.

C. Statistics

As used herein, the general form of a prediction rule consists in the specification of a function of one or multiple biomarkers potentially including clinical covariates to predict response or non-response, or more generally, predict benefit or lack of benefit in terms of suitably defined clinical endpoints.

The simplest form of a prediction rule consists of a univariate model without covariates, wherein the prediction is determined by means of a cutoff or threshold. This can be phrased in terms of the Heaviside function for a specific cutoff c and a biomarker measurement x, where the binary prediction A or B is to be made, then if $H(x-c)=0$, then predict A, if $H(x-c)=1$, then predict B.

This is the simplest way of using univariate biomarker measurements in prediction rules. If such a simple rule is sufficient, it allows for a simple identification of the direction of the effect, i.e., whether high or low expression levels are beneficial for the patient.

The situation can be more complicated if clinical covariates need to be considered and/or if multiple biomarkers are used in multivariate prediction rules. The two hypothetical examples below illustrate the issues involved:

Covariate Adjustment (Hypothetical Example)

For a biomarker X it is found in a clinical trial population that high expression levels are associated with a worse clinical response (univariate analysis). A closer analysis shows that there are two types of clinical response in the population, a first group which possesses a worse response than the second group and at the same time the biomarker expression for the first group is generally higher following administration of at least one dose of a VEGF antagonist (e.g., an anti-VEGF antibody, e.g., bevacizumab). An adjusted covariate analysis reveals that for each of the groups the relation of clinical benefit and clinical response is reversed, i.e., within the groups, lower expression levels are associated with better clinical response. The overall opposite effect was masked by the covariate type—and the covariate adjusted analysis as part of the prediction rule reversed the direction.

Multivariate Prediction (Hypothetical Example)

For a biomarker X it is found in a clinical trial population that high expression levels are slightly associated with a worse clinical response (univariate analysis). For a second biomarker Y a similar observation was made by univariate analysis. The combination of X and Y revealed that a good clinical response is seen if both biomarkers are low. This makes the rule to predict benefit if both biomarkers are below some cutoffs (AND—connection of a Heaviside prediction function). For the combination rule, a simple rule no longer applies in a univariate sense; for example, having low expression levels in X will not automatically predict a better clinical response.

These simple examples show that prediction rules with and without covariates cannot be judged on the univariate level of each biomarker. The combination of multiple biomarkers plus a potential adjustment by covariates does not allow assigning simple relationships to single biomarkers. Since the marker genes, in particular in serum, may be used in multiple-marker prediction models potentially including other clinical covariates, the direction of a beneficial effect of a single marker gene within such models cannot be determined in a simple way, and may contradict the direction found in univariate analyses, i.e., the situation as described for the single marker gene.

A clinician may use any of several methods known in the art to measure the effectiveness of a particular dosage scheme of a VEGF antagonist (e.g., an anti-VEGF antibody, e.g., bevacizumab). For example, in vivo imaging (e.g., MRI) can be used to determine the tumor size and to identify any metastases to determine relative effective responsiveness to the therapy. Dosage regimens may be adjusted to provide the optimum desired response (e.g., a therapeutic response). For example, a dose may be administered, several divided doses may be administered over time or the dose may be proportionally reduced or increased as indicated by exigencies of the therapeutic situation.

IV. Treatment with the VEGF Antagonist

A. Dosage and Administration

Once a patient responsive or sensitive to treatment with a VEGF antagonist (e.g., an anti-VEGF antibody, e.g., bevacizumab) as described herein has been identified, treatment with the VEGF antagonist, alone or in combination with other medicaments, can be carried out. Such treatment may result in, for example, a reduction in tumor size (e.g., glioblastoma tumor size) or an increase in progression free survival (PFS) and/or overall survival (OS). Moreover, treatment with the combination of a VEGF antagonist (e.g., an anti-VEGF antibody, e.g., bevacizumab) and at least one second medicament(s) preferably results in an additive, more preferably synergistic (or greater than additive), therapeutic benefit to the patient. Preferably, in this combination method the timing between at least one administration of the second medicament and at least one administration of the antagonist herein is about one month or less, more preferably, about two weeks or less.

It will be appreciated by those of skill in the medical arts that the exact manner of administering a therapeutically effective amount of a VEGF antagonist (e.g., an anti-VEGF antibody, e.g., bevacizumab) to a patient following diagnosis of their likely responsiveness to the VEGF antagonist will be at the discretion of the attending physician. The mode of administration, including dosage, combination with other agents, timing and frequency of administration, and the like, may be affected by the diagnosis of a patient's likely responsiveness to such VEGF antagonist, as well as the patient's condition and history. Thus, even patients having glioblastomas who are predicted to be relatively insensitive to a VEGF antagonist may still benefit from treatment therewith, particularly in combination with other agents, including agents that may alter a patient's responsiveness to the antagonist.

A composition comprising a VEGF antagonist will be formulated, dosed, and administered in a fashion consistent with good medical practice. Factors for consideration in this context include the particular type of glioblastoma being treated (e.g., a newly diagnosed glioblastoma or a recurrent glioblastoma, a glioblastoma of the proneural type, a glioblastoma of the mesenchymal type, or a glioblastoma of the proliferative type), the particular mammal being treated (e.g., human), the clinical condition of the individual patient, the cause of the glioblastoma, the site of delivery of the agent, possible side-effects, the type of antagonist, the method of administration, the scheduling of administration, and other factors known to medical practitioners. The effective amount of the VEGF antagonist to be administered will be governed by such considerations.

A physician having ordinary skill in the art can readily determine and prescribe the effective amount of the pharmaceutical composition required, depending on such factors as the particular antagonist type. For example, the physician could start with doses of such a VEGF antagonist (e.g., an anti-VEGF antibody, e.g., bevacizumab), employed in the pharmaceutical composition at levels lower than that required in order to achieve the desired therapeutic effect and gradually increase the dosage until the desired effect is achieved. The effectiveness of a given dose or treatment regimen of the antagonist can be determined, for example, by assessing signs and symptoms in the patient using standard measures of efficacy.

In certain examples, the VEGF antagonist (e.g., an anti-VEGF antibody, e.g., bevacizumab) may be the only medicament administered to the subject (i.e., as a monotherapy).

In certain examples, the patient is treated with the same VEGF antagonist (e.g., an anti-VEGF antibody, e.g., bevacizumab) at least twice. Thus, the initial and second VEGF antagonist exposures are preferably with the same antagonist, and more preferably all VEGF antagonist exposures are with the same VEGF antagonist, i.e., treatment for the first two exposures, and preferably all exposures, is with one type of VEGF antagonist, for example, an antagonist that binds to VEGF, such as an anti-VEGF antibody, e.g., all with bevacizumab.

As a general proposition, the effective amount of the VEGF antagonist administered parenterally per dose will be in the range of about 20 mg to about 5000 mg, by one or more dosages. Exemplary dosage regimens for antibodies, such as anti-VEGF antibodies (e.g., bevacizumab), include 100 or 400 mg every 1, 2, 3, or 4 weeks or is administered a dose of about 1, 3, 5, 10, 15, or 20 mg/kg every 1, 2, 3, or 4 weeks. For example, an effective amount of an anti-VEGF antibody (e.g., bevacizumab) can be administered at 10 mg/kg every two weeks, optionally, by intravenous (i.v.) administration. In another example, an effective amount of an anti-VEGF antibody can be administered at 15 mg/kg every three weeks, optionally, by i.v. administration. The dose may be administered as a single dose or as multiple doses (e.g., 2 or 3 doses), such as infusions.

In some instances, depending on the type and severity of the disease, about 1 ug/kg to 100 mg/kg (e.g., 0.1-20 mg/kg) of the VEGF antagonist (e.g., anti-VEGF antibody, e.g., bevacizumab) as an initial candidate dosage for administration to the subject, whether, for example, by one or more separate administrations, or by continuous infusion. In one embodiment, desirable dosages include, for example, 6 mg/kg, 8 mg/kg, 10 mg/kg, and 15 mg/kg. For repeated administrations or cycles over several days or longer, depending on the condition, the treatment is sustained until the cancer is treated, as measured by the methods described above or known in the art. However, other dosage regimens may be useful. In one example, the anti-VEGF antibody is administered once every week, every two weeks, or every three weeks, at a dose range from about 6 mg/kg to about 15 mg/kg, including but not limited to 6 mg/kg, 8 mg/kg, 10 mg/kg or 15 mg/kg. The progress of the therapy of the invention is easily monitored by conventional techniques and assays. In other embodiments, such dosing regimen is used in combination with a chemotherapy regimen in glioblastoma.

If multiple exposures of VEGF antagonist are provided, each exposure may be provided using the same or a different administration means. In one embodiment, each exposure is by intravenous administration. In another embodiment, each exposure is given by subcutaneous administration. In yet another embodiment, the exposures are given by both intravenous and subcutaneous administration.

In one embodiment, the VEGF antagonist (e.g., an anti-VEGF antibody, e.g., bevacizumab) is administered as a slow intravenous infusion rather than an intravenous push or bolus. For example, a steroid such as prednisolone or methylprednisolone (e.g., about 80-120 mg i.v., more specifically about 100 mg i.v.) is administered about 30 minutes prior to any infusion of the anti-VEGF antibody. For example, an anti-VEGF antibody such as bevacizumab can be infused through a dedicated line.

For the initial dose of a multi-dose exposure to VEGF antagonist (e.g., an anti-VEGF antibody, e.g., bevacizumab), or for the single dose if the exposure involves only one dose, such infusion is preferably commenced at a rate of about 50 mg/hour. This may be escalated, e.g., at a rate of about 50 mg/hour increments every about 30 minutes to a maximum of about 400 mg/hour. However, if the subject is experiencing an infusion-related reaction, the infusion rate is preferably reduced, e.g., to half the current rate, e.g., from 100 mg/hour to 50 mg/hour. For example, the infusion of such dose of VEGF antagonist (e.g., an about 1000-mg total dose) is completed at about 255 minutes (4 hours 15 min.). Optionally, the subjects receive a prophylactic treatment of acetaminophen/paracetamol (e.g., about 1 g) and diphenhydramine HCl (e.g., about 50 mg or equivalent dose of similar agent) by mouth about 30 to 60 minutes prior to the start of an infusion.

If more than one infusion (dose) of VEGF antagonist (e.g., an anti-VEGF antibody, e.g., bevacizumab) is given to achieve the total exposure, the second or subsequent VEGF antagonist infusions in this embodiment are commenced at a higher rate than the initial infusion, e.g., at about 100 mg/hour. This rate may be escalated, e.g., at a rate of about 100 mg/hour increments every about 30 minutes to a maximum of about 400 mg/hour. Subjects who experience an infusion-related reaction preferably have the infusion rate reduced to half that rate, e.g., from 100 mg/hour to 50 mg/hour. Preferably, the infusion of such second or subsequent dose of VEGF antagonist (e.g., an about 1000-mg total dose) is completed by about 195 minutes (3 hours 15 minutes).

In one embodiment, the VEGF antagonist is an anti-VEGF antibody (e.g., bevacizumab) and is administered in a dose of about 0.4 to 4 grams, and more preferably the antibody is administered in a dose of about 0.4 to 1.3 grams at a frequency of one to four doses within a period of about one month. Still more preferably, the dose is about 500 mg to 1.2 grams, and in other embodiments is about 750 mg to 1.1 grams. In such aspects, the VEGF antagonist is preferably administered in two to three doses, and/or is administered within a period of about 2 to 3 weeks.

The duration of therapy can be continued for as long as medically indicated or until a desired therapeutic effect (e.g., those described herein) is achieved. In certain embodiments, the therapy is continued for 1 month, 2 months, 4 months, 6 months, 8 months, 10 months, 1 year, 2 years, 3 years, 4 years, 5 years, or for a period of years up to the lifetime of the subject.

As noted above, however, these suggested amounts of VEGF antagonist are subject to a great deal of therapeutic discretion. The key factor in selecting an appropriate dose and scheduling is the result obtained, as indicated above. In some embodiments, the VEGF antagonist is administered as close to the first sign, diagnosis, appearance, or occurrence of the glioblastoma as possible.

1. Routes of Administration

The VEGF antagonist (e.g., an anti-VEGF antibody, e.g., bevacizumab) can be administered by any suitable means, including parenteral, topical, subcutaneous, intraperitoneal, intrapulmonary, intranasal, and/or intralesional administration. Parenteral infusions include intramuscular, intravenous, intraarterial, intraperitoneal, or subcutaneous administration. Intrathecal administration is also contemplated. In addition, the VEGF antagonist may suitably be administered by pulse infusion, e.g., with declining doses of the VEGF antagonist. Most preferably, the dosing is given by intravenous injections.

If multiple exposures of anti-VEGF antibody are provided, each exposure may be provided using the same or a different administration means. In one embodiment, each exposure is by intravenous (i.v.) administration. For example, an anti-VEGF antibody, such as bevacizumab, can be infused through a dedicated line. For example, an anti-VEGF antibody, such as bevacizumab, can be administered initially intravenously over about 90 minutes, with subsequent infusions over about 60 minutes and then about 30 minutes. In another embodiment, each exposure is given by subcutaneous (s.c.) administration. In yet another embodiment, the exposures are given by both i.v. and s.c. administration.

Aside from administration of VEGF antagonists to the patient by traditional routes as noted above, the present invention includes administration by gene therapy. See, for example, WO 1996/07321, concerning the use of gene therapy to generate intracellular antibodies.

There are two major approaches to getting the nucleic acid (optionally contained in a vector) into the patient's cells: in vivo and ex vivo. For in vivo delivery the nucleic acid is injected directly into the patient, usually at the site where the antagonist is required. For ex vivo treatment, the patient's cells are removed, the nucleic acid is introduced into these isolated cells and the modified cells are administered to the patient either directly, or, for example, encapsulated within porous membranes which are implanted into the patient (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). In some situations it is desirable to provide the nucleic acid source with an agent specific for the target cells, such as an antibody specific for a cell-surface membrane protein on the target cell, a ligand for a receptor on the target cell, etc. Where liposomes are employed, proteins that bind to a cell-surface membrane protein associated with endocytosis may be used for targeting and/or to facilitate uptake, e.g., capsid proteins or fragments thereof tropic for a particular cell type, antibodies for proteins that undergo internalization in cycling, and proteins that target intracellular localization and enhance intracellular half-life. The technique of receptor-mediated endocytosis is described, for example, by Wu et al., *J. Biol. Chem.* 262: 4429-4432 (1987); and Wagner et al., *PNAS USA* 87:3410-3414 (1990). Gene-marking and gene-therapy protocols are described, for example, in Anderson et al., *Science* 256:808-813 (1992) and WO 1993/25673.

2. Combination Therapy

In some embodiments, a VEGF antagonist (e.g., anti-VEGF antibody, e.g., bevacizumab) may be used in combination with one or more additional anti-cancer agents or therapies. Examples of anti-cancer therapies include, without limitation, surgery, radiation therapy (radiotherapy), biotherapy, immunotherapy, chemotherapy (e.g., with temozolomide (TMZ)), or a combination of these therapies. In addition, cytotoxic agents, anti-angiogenic and anti-proliferative agents can be used in combination with the anti-VEGF antibody. The one or more additional anti-cancer agents or therapies preferably have complementary activities to the VEGF antagonist such that they do not adversely affect each other. The combined administration includes co-administration, using separate formulations or a single pharmaceutical formulation, and consecutive administration in either order, wherein preferably there is a time period while both (or all) active agents simultaneously exert their biological activities.

The one or more additional anti-cancer agent may be a chemotherapeutic agent, a cytotoxic agent, a cytokine, a growth inhibitory agent, an anti-hormonal agent, and combinations thereof. Such molecules are suitably present in combination in amounts that are effective for the purpose intended. A pharmaceutical composition containing a VEGF antagonist (e.g., an anti-VEGF antibody, e.g., bevacizumab) may also comprise a therapeutically effective amount of an anti-neoplastic agent, a chemotherapeutic agent a growth inhibitory agent, a cytotoxic agent, or combinations thereof.

In one aspect, the first compound is an anti-VEGF antibody and the at least one additional compound is a therapeutic antibody other than an anti-VEGF antibody. In one embodiment, the at least one additional compound is an antibody that binds a cancer cell surface marker. In one embodiment the at least one additional compound is an anti-HER2 antibody, trastuzumab (e.g., Herceptin®, Genentech, Inc., South San Francisco, Calif.). In one embodiment the at least one additional compound is an anti-HER2 antibody, pertuzumab (Omnitarg™, Genentech, Inc., South San Francisco, Calif., see U.S. Pat. No. 6,949,245). In an embodiment, the at least one additional compound is an antibody (either a naked antibody or an ADC), and the additional antibody is a second, third, fourth, fifth, sixth antibody or more, such that a combination of such second, third, fourth, fifth, sixth, or more antibodies (either naked or as an ADC) is efficacious in treating an angiogenic disorder.

Other therapeutic regimens in accordance with this invention may include administration of an anti-cancer agent and, including without limitation radiation therapy and/or bone marrow and peripheral blood transplants, and/or a cytotoxic agent, a chemotherapeutic agent, or a growth inhibitory agent. In one of such embodiments, a chemotherapeutic agent is an agent or a combination of agents such as, for example, cyclophosphamide, hydroxydaunorubicin, adriamycin, doxorubincin, vincristine (ONCOVIN™) prednisolone, CHOP, CVP, or COP, or immunotherapeutics such as anti-PSCA, anti-HER2 (e.g., HERCEPTIN®, OMNITARG™). In another embodiment, the combination includes docetaxel, doxorubicin, and cyclophosphamide. The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

In one embodiment, treatment with a VEGF antagonist (e.g., an anti-VEGF antibody) involves the combined administration of an anti-cancer agent identified herein, and one or more chemotherapeutic agents or growth inhibitory agents, including coadministration of cocktails of different chemotherapeutic agents. Chemotherapeutic agents include taxanes (such as paclitaxel and docetaxel) and/or anthracycline antibiotics. Preparation and dosing schedules for such chemotherapeutic agents may be used according to manufacturer's instructions or as determined empirically by the skilled practitioner. Preparation and dosing schedules for such chemotherapy are also described in "Chemotherapy Service," (1992) Ed., M. C. Perry, Williams & Wilkins, Baltimore, Md.

Suitable dosages for any of the above co-administered agents are those presently used and may be lowered due to the combined action (synergy) of the VEGF antagonist and other chemotherapeutic agents or treatments.

The combination therapy may provide "synergy" and prove "synergistic," i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

In general, for the prevention or treatment of disease, the appropriate dosage of the additional therapeutic agent will depend on the type of disease to be treated, the type of antibody, the severity and course of the disease, whether the VEGF antagonist (e.g., an anti-VEGF antibody, e.g., bevacizumab) and additional agent (e.g., TMZ) are administered for preventive or therapeutic purposes, previous therapy, the patient's clinical history and response to the VEGF antagonist and additional agent, and the discretion of the attending physician. The VEGF antagonist and additional agent are suitably administered to the patient at one time or over a series of treatments. The VEGF antagonist is typically administered as set forth above. Depending on the type and severity of the disease, about 20 mg/m$^2$ to 600 mg/m$^2$ of the additional agent is an initial candidate dosage for administration to the patient, whether, for example, by one or more separate administrations, or by continuous infusion. One typical daily dosage might range from about or about 20 mg/m$^2$, 85 mg/m$^2$, 90 mg/m$^2$, 125 mg/m$^2$, 200 mg/m$^2$, 400 mg/m$^2$, 500 mg/m$^2$ or more, depending on the factors mentioned above. For repeated administrations over several days or longer, depending on the condition, the treatment is sustained until a desired suppression of disease symptoms occurs. Thus, one or more doses of about 20 mg/m$^2$, 85 mg/m$^2$, 90 mg/m$^2$, 125 mg/m$^2$, 200 mg/m$^2$, 400 mg/m$^2$, 500 mg/m$^2$, 600 mg/m$^2$ (or any combination thereof) may be administered to the patient. Such doses may be administered intermittently, e.g., every week or every two, three weeks, four, five, or six (e.g., such that the patient receives from about two to about twenty, e.g., about six doses of the additional agent). An initial higher loading dose, followed by one or more lower doses may be administered. However, other dosage regimens may be useful. The progress of this therapy is easily monitored by conventional techniques and assays.

In one embodiment, the subject has never been previously administered any drug(s) to treat glioblastoma. In another embodiment, the subject or patient has been previously administered one or more medicaments(s) to treat glioblastoma. In a further embodiment, the subject or patient was not responsive to one or more of the medicaments that had been previously administered. Such drugs to which the subject may be non-responsive include, for example, anti-neoplastic agents, chemotherapeutic agents, cytotoxic agents, and/or growth inhibitory agents. More particularly, the drugs to which the subject may be non-responsive include VEGF antagonists, such as anti-VEGF antibodies (e.g., bevacizumab). In a further aspect, such VEGF antagonists include an antibody or immunoadhesin, such that re-treatment is contemplated with one or more antibodies or immunoadhesins to which the subject was formerly non-responsive.

B. VEGF Antagonist

In all the methods set forth herein, the VEGF antagonist may be an anti-VEGF antibody.

In certain embodiments, the anti-VEGF antibody may be a chimeric antibody. Certain chimeric antibodies are described, e.g., in U.S. Pat. No. 4,816,567; and Morrison et al., PNAS USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, the anti-VEGF antibody may be a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity. Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing SDR (a-CDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

In certain embodiments, the anti-VEGF antibody may be a human antibody. Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20:450-459 (2008). Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region. Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).) Human antibodies generated via human B-cell hybridoma technology are also described in Li et al., PNAS USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005).

In certain embodiments, the anti-VEGF antibody may be, or have been, isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in Methods in Molecular Biology 178:1-37 (O'Brien et al., ed., Human Press, Totowa, N.J., 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, N.J., 2003); Sidhu et al., J. Mol. Biol. 338(2): 299-310 (2004); Lee et al., J. Mol. Biol. 340(5): 1073-1093 (2004); Fellouse, PNAS USA 101(34): 12467-12472 (2004); and Lee et al., J. Immunol. Methods 284(1-2): 119-132 (2004).

In some phage display methods, repertoires of VH and VL genes are separately cloned by polymerase chain reaction (PCR) and recombined randomly in phage libraries, which can then be screened for antigen-binding phage as described in Winter et al., Ann. Rev. Immunol., 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., EMBO J, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, J. Mol. Biol., 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

In some embodiments, anti-VEGF antibodies that are useful in the methods of the invention include any antibody, or antigen binding fragment thereof, that bind with sufficient affinity and specificity to VEGF and can reduce or inhibit the biological activity of VEGF. An anti-VEGF antibody will usually not bind to other VEGF homologues such as VEGF-B or VEGF-C, nor other growth factors such as PIGF, PDGF, or bFGF. For example, in certain embodiments of the invention, the anti-VEGF antibodies include, but are not limited to, a monoclonal antibody that binds to the same epitope as the monoclonal anti-VEGF antibody A4.6.1 produced by hybridoma ATCC HB 10709; a recombinant humanized anti-VEGF monoclonal antibody generated according to Presta et al. (1997) Cancer Res. 57:4593-4599. In one embodiment, the anti-VEGF antibody is bevacizumab (BV or Bev), also known as "rhuMAb VEGF" or "AVASTIN®." It comprises mutated human IgG1 framework regions and antigen-binding complementarity-determining regions from the murine anti-hVEGF monoclonal antibody A.4.6.1 that blocks binding of human VEGF to its receptors. Approximately 93% of the amino acid sequence of bevacizumab, including most of the framework regions, is derived from human IgG1, and about 7% of the sequence is derived from the murine antibody A4.6.1. Bevacizumab and other humanized anti-VEGF antibodies are described in U.S. Pat. No. 6,884,879 issued Feb. 26, 2005. Additional antibodies include the G6 or B20 series antibodies (e.g., G6-31, B20-4.1), as described in PCT Publication No. WO2005/012359, PCT Publication No. WO2005/044853, and U.S. Patent Application 60/991,302, the content of these patent applications are expressly incorporated herein by reference. For additional antibodies see U.S. Pat. Nos. 7,060,269, 6,582,959, 6,703,020; 6,054,297; WO98/45332; WO 96/30046; WO94/10202; EP 0666868B1; U.S. Patent Application Publication Nos. 2006009360, 20050186208, 20030206899, 20030190317, 20030203409, and 20050112126; and Popkov et al., Journal of Immunological Methods 288:149-164 (2004). Other antibodies include those that bind to a functional epitope on human VEGF comprising of residues F17, M18, D19, Y21, Y25, Q89, I191, K101, E103, and C104 or, alternatively, comprising residues F17, Y21, Q22, Y25, D63, I83 and Q89.

In some embodiments, an anti-VEGF antibody useful in any one of the methods described herein may have a light chain variable region comprising the following amino acid sequence:

DIQMTQSPSS LSASVGDRVT ITCSASQDIS NYLNWYQQKP GKAPKVLIYF TSSLHSGVPS RFSGSGSGTD FTLTISSLQP EDFATYYCQQ YSTVPWTFGQ GTKVEIKR (SEQ ID NO: 1), and a heavy chain variable region comprising the following amino acid sequence:

EVQLVESGGG LVQPGGSLRL SCAASGYTFT NYGMNWVRQA PGKGLEWVGW INTYTGEPTY AADFKRRFTF SLDTSKSTAY LQMNSLRAED TAVYYCAKYP HYYGSSHWYF DVWGQGTLVT VSS (SEQ ID NO: 2).

The anti-VEGF antibody herein may be a chimeric, humanized, or human antibody, and may, for example, be bevacizumab.

In yet other embodiments, the anti-VEGF antibody may be unconjugated, such as a naked anti-VEGF antibody, or may be conjugated with another molecule for further effectiveness, such as, for example, to improve half-life.

V. Pharmaceutical Formulations

Therapeutic formulations of the antagonists used in accordance with the present invention are prepared for storage by mixing the antagonist having the desired degree of purity with optional pharmaceutically acceptable carriers, excipients, or stabilizers in the form of lyophilized formulations or aqueous solutions. For general information concerning formulations, see, e.g., Gilman et al., (eds.) (1990), *The Pharmacological Bases of Therapeutics,* 8th Ed., Pergamon Press; A. Gennaro (ed.), Remington's Pharmaceutical Sciences, 18th Edition, (1990), Mack Publishing Co., Eastori, Pa.; Avis et al., (eds.) (1993) *Pharmaceutical Dosage Forms: Parenteral Medications* Dekker, New York; Lieberman et al., (eds.) (1990) *Pharmaceutical Dosage Forms: Tablets* Dekker, New York; and Lieberman et al., (eds.) (1990), *Pharmaceutical Dosage Forms: Disperse Systems* Dekker, New York, Kenneth A. Walters (ed.) (2002) *Dermatological and Transdermal Formulations* (Drugs and the Pharmaceutical Sciences), Vol 119, Marcel Dekker.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™, or polyethylene glycol (PEG).

Exemplary anti-VEGF antibody formulations are described in U.S. Pat. No. 6,884,879. In certain embodiments anti-VEGF antibodies are formulated at 25 mg/mL in single use vials. In certain embodiments, 100 mg of the anti-VEGF antibodies are formulated in 240 mg $\alpha,\alpha$-trehalose dihydrate, 23.2 mg sodium phosphate (monobasic, monohydrate), 4.8 mg sodium phosphate (dibasic anhydrous), 1.6 mg polysorbate 20, and water for injection, USP. In certain embodiments, 400 mg of the anti-VEGF antibodies are formulated in 960 mg $\alpha,\alpha$-trehalose dihydrate, 92.8 mg sodium phosphate (monobasic, monohydrate), 19.2 mg sodium phosphate (dibasic anhydrous), 6.4 mg polysorbate 20, and water for injection, USP.

Lyophilized formulations adapted for subcutaneous administration are described, for example, in U.S. Pat. No. 6,267,958. Such lyophilized formulations may be reconstituted with a suitable diluent to a high protein concentration and the reconstituted formulation may be administered subcutaneously to the mammal to be treated herein.

Crystallized forms of the antagonist are also contemplated. See, for example, US 2002/0136719A1.

The formulation herein may also contain more than one active compound (a second medicament as noted above), preferably those with complementary activities that do not adversely affect each other. The type and effective amounts of such medicaments depend, for example, on the amount and type of VEGF antagonist (e.g., an anti-VEGF antibody, e.g., bevacizumab) present in the formulation, and clinical parameters of the subjects. The preferred such second medicaments are noted above.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antagonist, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

EXAMPLES

The following examples are provided to illustrate, but not to limit the presently claimed invention.

Example 1. Statistical Methods and Microarray Analysis

Statistical Methods

The statistical tasks can, in general, comprise the following steps:
1. Pre-selection of candidate biomarkers
2. Pre-selection of relevant clinical efficacy response predictive covariates
3. Selection of biomarker prediction functions at a univariate level
4. Selection of biomarker prediction functions including clinical covariates at a univariate level
5. Selection of biomarker prediction functions at a multivariate level
6. Selection of biomarker prediction functions including clinical covariates at a multivariate level The following text details the different steps:

1. Pre-Selection of Candidate Biomarkers

The statistical pre-selection of candidate biomarkers is oriented towards the strength of association with measures of clinical benefit. For this purpose the different clinical endpoints may be transformed in derived surrogate scores, as, e.g., an ordinal assignment of the degree of clinical benefit scores regarding TTP that avoid censored observations. These surrogate transformed measures can be easily used for simple correlation analysis, e.g., by the non-parametric Spearman rank correlation approach. An alternative is to use the biomarker measurements as metric covariates in time-to-event regression models, as, e.g., Cox proportional hazard regression. Depending on the statistical distribution of the biomarker values, this step may require some pre-processing, as, for example, variance-stabilizing transformations and the use of suitable scales or, alternatively, a standardization step such as using percentiles instead of raw measurements. A further approach is inspection of bivariate scatter plots, for example, by displaying the scatter of (x-axis=biomarker value, y-axis=measure of clinical benefit) on a single-patient basis. Some non-parametric regression line as achieved, for example, by smoothing splines can be useful to visualize the association of biomarker and clinical benefit.

The goal of these different approaches is the pre-selection of biomarker candidates that show some association with clinical benefit in at least one of the benefit measures employed, while results for other measures are not contradictory. When there are available control groups, then differences in association of biomarkers with clinical benefit in the different arms could be a sign of differential prediction that makes the biomarker(s) eligible for further consideration.

2. Pre-Selection of Relevant Clinical Efficacy Response Predictive Covariates

The statistical pre-selection of clinical covariates as defined herein parallels the approaches for pre-selecting biomarkers and is also oriented towards the strength of association with measures of clinical benefit. So in principle the same methods apply as considered under 1 above. In addition to statistical criteria, criteria from clinical experience and theoretical knowledge may apply to pre-select relevant clinical covariates.

The predictive value of clinical covariates could interact with the predictive value of the biomarkers. They will be considered for refined prediction rules, if necessary.

3. Selection of Biomarker Prediction Functions at a Univariate Level

The term "prediction function" will be used in a general sense to mean a numerical function of a biomarker measurement that results in a number scaled to imply the target prediction.

A simple example is the choice of the Heaviside function for a specific cutoff c and a biomarker measurement x, where the binary prediction A or B is to be made, then if f H (x−c)=0, then predict A, if H (x−c)=1, then predict B.

This is probably the most common way of using univariate biomarker measurements in prediction rules. The definition of "prediction function" as noted above includes referral to an existing training data set that can be used to explore the prediction possibilities. Different routes can be taken to achieve a suitable cutoff c from the training set. First, the scatterplot with smoothing spline mentioned under 1 can be used to define the cutoff. Alternatively, some percentile of the distribution could be chosen, e.g., the median or a quartile. Cutoffs can also be systematically extracted by investigating all possible cutoffs according to their prediction potential with regard to the measures of clinical benefit. Then, these results can be plotted to allow for an either manual selection or to employ some search algorithm for optimality. This can be realized based on certain clinical endpoints using a Cox model, wherein at each test cutoff the biomarker is used as a binary covariate. Then the results for the clinical endpoints can be considered together to chose a cutoff that shows prediction in line with both endpoints.

Another uncommon approach for choosing a prediction function can be based on a fixed-parameter Cox regression model obtained from the training set with biomarker values (possibly transformed) as covariate. A further possibility is to base the decision on some likelihood ratio (or monotonic transform of it), where the target probability densities are pre-determined in the training set for separation of the prediction states. Then the biomarker would be plugged into some function of predictive criteria.

4. Selection of Biomarker Prediction Functions Including Clinical Covariates at a Univariate Level Univariate refers to using only one biomarker—with regard to clinical covariates, this can be a multivariate model. This approach parallels the search without clinical covariates, except that the methods should allow for incorporating the relevant covariate information. The scatterplot method of choosing a cutoff allows only a limited use of covariates, e.g., a binary covariate could be color coded within the plot. If the analysis relies on some regression approach, then the use of covariates (also many of them at a time) is usually facilitated. The cutoff search based on the Cox model described under 3 above allows for an easy incorporation of covariates and thereby leads to a covariate adjusted univariate cutoff search. The adjustment by covariates may be done as covariates in the model or via the inclusion in a stratified analysis.

Also the other choices of prediction functions allow for the incorporation of covariates.

This is straightforward for the Cox model choice as prediction function. This includes the option to estimate the influence of covariates on an interaction level, which means that, e.g., for different age groups different predictive criteria apply.

For the likelihood ratio type of prediction functions, the prediction densities must be estimated including covariates. For this purpose, the methodology of multivariate pattern recognition can be used or the biomarker values can be adjusted by multiple regression on the covariates (prior to density estimation).

The CART technology (*Classification and Regression Trees*; Breiman et al. (Wadsworth, Inc.: New York, 1984) can be used for this purpose, employing a biomarker (raw measurement level) plus clinical covariates and utilizing a clinical benefit measure as response. Cutoffs are searched and a decision-tree type of function will be found involving the covariates for prediction. The cutoffs and algorithms chosen by CART are frequently close to optimal and may be combined and unified by considering different clinical benefit measures.

5. Selection of Biomarker Prediction Functions at a Multivariate Level

When there are several biomarker candidates that maintain their prediction potential within the different univariate prediction function choices, then a further improvement may be achieved by combinations of biomarkers, i.e., considering multivariate prediction functions.

Based on the simple Heaviside function model, combinations of biomarkers may be evaluated, e.g., by considering bivariate scatterplots of biomarker values where optimal cutoffs are indicated. Then a combination of biomarkers can be achieved by combining different Heaviside function by the logical "AND" and "OR" operators to achieve an improved prediction.

The CART technology can be used for this purpose, employing multiple biomarkers (raw measurement level) and a clinical benefit measure as response, to achieve cutoffs for biomarkers and decision-tree type of functions for prediction. The cutoffs and algorithms chosen by CART are frequently close to optimal and may be combined and unified by considering different clinical benefit measures.

The Cox-regression can be employed on different levels. A first way is to incorporate the multiple biomarkers in a binary way (i.e., based on Heaviside functions with some cutoffs). The other option is to employ biomarkers in a metric way (after suitable transformations), or a mixture of the binary and metric approach. The evolving multivariate prediction function is of the Cox type as described under 3 above.

The multivariate likelihood ratio approach is difficult to implement, but presents another option for multivariate prediction functions.

6. Selection of Biomarker Prediction Functions Including Clinical Covariates at a Multivariate Level When there are relevant clinical covariates, then a further improvement may be achieved by combining multiple biomarkers with multiple clinical covariates. The different prediction function choices will be evaluated with respect to the possibilities to include clinical covariates.

Based on the simple logical combinations of Heaviside functions for the biomarkers, further covariates may be included to the prediction function based on the logistic regression model obtained in the training set.

The CART technology and the evolving decision trees can be easily used with additional covariates, which would include these in the prediction algorithm.

All prediction functions based on the Cox-regression can use further clinical covariates. The option exists to estimate the influence of covariates on an interaction level, which means that, e.g., for different age groups different predictive criteria apply.

The multivariate likelihood ratio approach is not directly extendible to the use of additional covariates.

Microarray Analysis

All analyses steps were performed using the open source programming language R(R Core Team (2013) *R: A Language and Environment for Statistical Computing*. R Foundation for Statistical Computing, Vienna, Austria). Raw data from all Affymetrix microarrays was normalized to a common reference distribution using the RefPlus R package (Harbron et al. *Bioinformatics*. 23(18): 2493-2494, 2007).

Example 2. AvaGlio Study

The AvaGlio trial evaluated the efficacy and safety of bevacizumab in combination temozolomide and radiotherapy for newly diagnosed glioblastoma. This study was designed as a prospective, randomized, double blind, placebo controlled Phase III evaluation of bevacizumab plus chemotherapy versus chemotherapy alone. To be eligible, patients must have had newly diagnosed glioblastoma with a tissue diagnosis that has been established following either a surgical resection or biopsy. By adding bevacizumab to chemotherapy and radiotherapy, the AvaGlio trial aimed to improve overall survival (OS) and progression-free survival (PFS) for this group of patients who had limited therapeutic options and faced a particularly poor prognosis. The primary objective was to compare OS and PFS of patients randomized to temozolomide (TMZ) and radiotherapy only or to temozolomide and radiotherapy plus bevacizumab.

Overview of AvaGlio Study

This trial consisted of three phases (Concurrent, Maintenance, and Monotherapy) and two (2) treatment arms: TMZ and radiotherapy (Arm 1), and TMZ and radiotherapy plus bevacizumab (Arm 2). Patients were randomly assigned (1:1) to either arm.

Arm 1 (chemotherapy and radiotherapy alone): Eligible patients received 2 Gy radiotherapy 5 days a week for 6 weeks and 75 mg/m$^2$ TMZ orally daily for 6 weeks from the first day to the last day of radiotherapy in combination with 10 mg/kg bevacizumab i.v. every 2 weeks. After a 4-week treatment break, eligible patients received 6 cycles of 150-200 mg/m$^2$ TMZ on days 1-5 of an every-4-week schedule in combination with 10 mg/kg placebo i.v. every 2 weeks. TMZ was administered orally starting with a 150 mg/m$^2$ dose that could be escalated. Placebo monotherapy (15 mg/kg every 3 weeks) was then continued until disease progression. Upon disease progression, patients were treated at the investigator's discretion.

Arm 2 (TMZ and radiotherapy plus bevacizumab): Eligible patients received 2 Gy radiotherapy 5 days a week for 6 weeks and 75 mg/m$^2$ TMZ orally daily for 6 weeks from the first day to the last day of radiotherapy in combination with 10 mg/kg bevacizumab i.v. every 2 weeks. After a 4-week treatment break, eligible patients received 6 cycles of 150-200 mg/m$^2$ TMZ on days 1-5 of an every-4-week schedule in combination with 10 mg/kg beveciumab i.v. every 2 weeks. TMZ was administered orally starting with a 150 mg/m$^2$ dose that could be escalated. Bevaciazumab monotherapy (15 mg/kg every 3 weeks) was then continued until disease progression. Upon disease progression, patients were treated at the investigator's discretion.

The initial bevacizumab infusion was over 90 minutes, with subsequent infusions over 60 minutes and then 30 minutes, as tolerated. Bevacizumab was administered on the last day of radiotherapy and TMZ treatment, i.e., the day before the start of the TMZ treatment break.

Analyses of PFS were based on tumor assessments MacDonald Response Criteria (modified WHO criteria) using MRI of the brain and a neurological evalution as described in Macdonald et al. (*J. Clin. Oncol.* 8: 1277-80, 1990). Tumor assessments were performed at baseline, at the end of the 4-week treatment break, then every 8 weeks.

Study Population—Inclusion Criteria

Patients≥8 years of age and with newly diagnosed supratentorial Glioblastoma (GBM) with a tissue diagnosis that had been established following either a surgical resection or biopsy were included. This includes treatment-naïve chemotherapy and radiotherapy patients with prior diagnosis of a lower grade astrocytoma that had been upgraded to a histologically verified GBM. Patients must have had WHO performance status 2.

Study Population—Exclusion Criteria

Evidence of recent hemorrhage on post-operative MRI of the brain excluded candidate patients. However, patients with clinically asymptomatic presence of hemosiderin, resolving hemorrhagic changes related to surgery, and presence of punctate hemorrhage in the tumor were permitted entry into the study. Previous centralized screening for MGMT status for enrollment into a clinical trial; any prior chemotherapy (including carmustine-containing wafers (Gliadel®) or immunotherapy (including vaccine therapy) for glioblastomas and low grade astrocytomas; any prior radiotherapy to the brain or prior radiotherapy resulting in a potential overlap in the radiation field; prior history of hypertensive crisis or hypertensive encephalopathy; history of grade 2 haemoptysis according to the NCI-CTC criteria within 1 month prior to randomization; evidence of bleeding diathesis or coagulopathy (in the absence of therapeutic anticoagulation); major surgical procedure, open biopsy, intracranial biopsy, ventriculoperitoneal shunt or significant traumatic injury within 28 days prior to randomization; core biopsy (excluding intracranial biopsy) or other minor surgical procedure within 7 days prior to randomization also excluded patients. Placement of a central vascular access device (CVAD) if performed within 2 days prior to bevacizumab/placebo administration; history of abdominal fistula or gastrointestinal perforation within 6 months prior to randomization history of intracranial abscess within 6 months prior to randomization; serious non-healing wound, active ulcer, or untreated bone fracture also excluded patients. With respect to pregnant or lactating females, serum pregnancy tests were assessed within 7 days prior to study treatment start, or within 14 days (with a confirmatory urine pregnancy test within 7 days prior to study treatment start). Also excluded were fertile women (defined as <2 years after last menstruation and not surgically sterile) and men not using highly-effective, hormonal or non-hormonal means of contraception (i.e., intrauterine contraceptive device); patients with a history of stroke or transient ischemic attack (TIA) within ≤6 months prior to randomization, inadequately controlled hypertension (sustained systolic>150 mmHg and/or diastolic>100 mmHg) or significant vascular disease, including aortic aneurism requiring surgical repair or recent peripheral arterial thrombosis, within ≤6 months prior to randomization. Also excluded were patients who had myocardial infarction or unstable angina within ≤6 months prior to randomization, New York Heart Association (NYHA) grade II or greater congestive heart failure (CHF), or known hypersensitivity to any of the study drugs or excipients.

Example 3. Unsupervised Identification of Gene Expression Subtypes

In an alternative approach toward assigning the gene expression subtypes originally described by Phillips et al. (*Cancer Cell.* 9(3): 157-173, 2006) to the samples from the AvaGlio trial, we performed an unsupervised analysis of the Nanostring gene expression data. In addition to the 35-probe signature, Phillips et al. had also identified a broader set of 725 Affymetrix microarray probes, at the time of writing mapped to 667 Entrez gene identifiers, corresponding to 556 unique annotated gene symbols. 108 of these genes, listed above in Table 1, were assayed on the Nanostring platform.

Next, we used this extended list of subtype-specific genes to perform an unsupervised analysis of the AvaGlio data. As has been reported in the literature, GBM patients carrying a gain-of-function mutation (R132MUT) in the IDH1 gene have a markedly better prognosis than patients with the IDH1 wildtype gene (Lai et al. *J. Clin. Oncol.* 29(34): 4482-90, 2011). Ten patients from the AvaGlio biomarker-available population (n=349) carry an IDH1(R132MUT) gain-of-function variant. These patients were excluded from the following analysis.

The raw Nanostring counts obtained from the nCounter analyzed software were log 2 transformed and normalized across samples by adjusting the mean and the standard deviation of the expression across all assayed probes to the same reference values. After normalization and transformation of the gene expression scores for these 108 genes into z-scores, we performed an unsupervised analysis ("clustering") of the AvaGlio samples into k=3 clusters using the Partitioning around medoids (PAM, Kaufman and Rousseeuw. *Clustering by Means of Medoids.* Reports of the Faculty of Mathematics and Informatics, Delft University of Technology, 1987). The clusters were not pre-specified, but were determined by the algorithm automatically instead. A small number of samples was clustered with a negative Silhouette width, indicating that their expression did not match the final cluster assignment; these samples were labeled "Unclassified" (FIG. 1). We assigned the labels "Proneural," "Mesenchymal," and "Proliferative" to the PAM clusters based on the highest expression of the signature genes of Phillips et al. (FIG. 1, row annotation).

Figure 2:
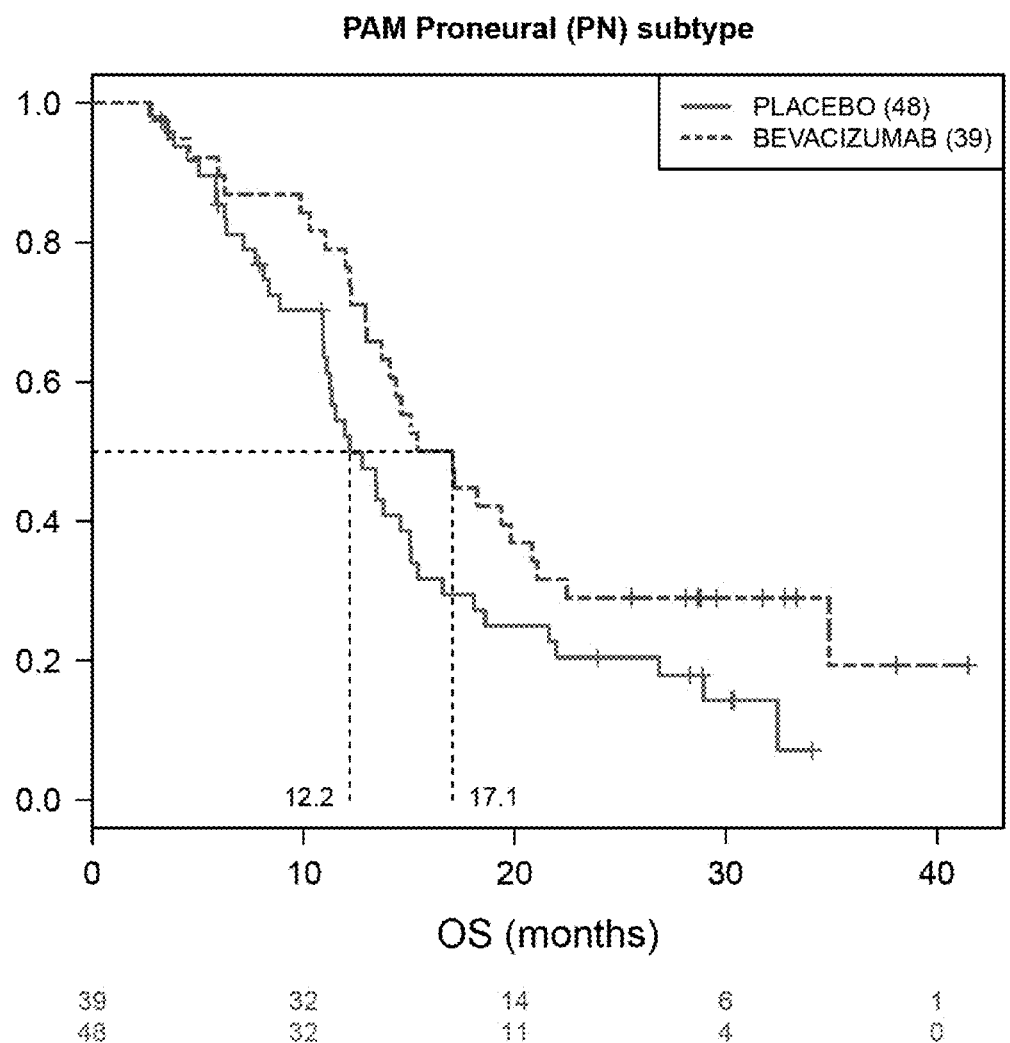
FIG. 2 is a Kaplan-Meier survival curve of patients assigned to the Proneural (PN) subtype using unsupervised analysis (PAM) in the two AvaGlio treatment arms (bevacizumab treatment arm: dashed line; placebo treatment arm: solid line). The number of patients at risk is indicated below the graph for the bevacizumab treatment (top row) and placebo treatment arms (bottom row).

To test for a predictive value of the Proneural (PN) cluster assignment, comprised of 85 samples, we performed a multivariate analysis of the effect of anti-VEGF therapy (e.g., anti-VEGF antibody therapy, e.g., bevacizumab therapy) in combination with RT and chemotherapy on OS in this subgroup, accounting for the main known clinical covariates (e.g., age, corticosteroids, extent of resection, gender, Karnofsky Performance Score (KPS), methylation status of O-6-methylguanine-DNA methyltransferase (MGMT) promoter, mini-mental state examination score (MMSE), recursive partitioning analysis (RPA) class, and WHO performance score)). The multivariate Cox PH indicates that anti-VEGF therapy resulted in a significant OS benefit for patients having PN subtype glioblastoma, but not for patients having non-PN subtype glioblastoma (FIG. 2). Specifically, for patients having PN subtype glioblastoma, median OS in the treatment arm was 17.1 months compared to 12.2 months in the placebo arm, with a HR equal to 0.42 (95% CI=0.23-0.78; p=0.006).

To define Nanostring-specific centroids for the three subtypes, we calculated the mean expression for each classifier gene for each of the three PAM clusters/subtypes (Table 4).

TABLE 4

Extended Nanostring-specific centroids for Phillips expression subtypes

| Gene Symbol | Proliferative | Proneural | Mesenchymal |
|---|---|---|---|
| ABHD6 | −0.045 | 0.844 | −0.283 |
| ACTN1 | 0.220 | −0.325 | 0.439 |
| ANGPT2 | 0.195 | −0.154 | 0.212 |
| ANGPTL4 | −0.268 | −0.294 | 0.549 |
| AP2B1 | 0.424 | 0.585 | −0.289 |
| ASCL1 | 0.545 | 0.729 | −0.748 |
| ATP6V1G2 | −0.089 | 0.658 | −0.607 |
| BCAN | 0.438 | 0.680 | −0.584 |
| BCL3 | −0.252 | −0.596 | 0.678 |
| BMP2 | −0.054 | 0.305 | −0.135 |
| BRIP1 | 0.948 | 0.156 | −0.569 |
| CA12 | −0.134 | −0.594 | 0.551 |
| CCNB1 | 0.856 | 0.122 | −0.287 |
| CCNE2 | 0.674 | 0.400 | −0.462 |
| CD274 | −0.353 | −0.622 | 0.469 |
| CDC6 | 0.588 | −0.184 | −0.529 |
| CDCA7 | 0.647 | 0.224 | −0.599 |
| CDKN2A | −0.053 | −0.210 | −0.118 |
| CDKN2C | 0.780 | 0.050 | −0.214 |
| CENPK | 1.031 | 0.072 | −0.440 |
| CHEK1 | 0.933 | 0.199 | −0.478 |
| CHI3L1 | −0.158 | −0.536 | 0.623 |
| CNTN3 | −0.427 | 0.467 | −0.363 |
| COL4A1 | 0.017 | −0.284 | 0.393 |
| COL4A2 | 0.038 | −0.358 | 0.400 |
| CRYAB | −0.228 | 0.527 | −0.080 |
| CSDC2 | −0.172 | 0.617 | −0.462 |
| CSMD3 | −0.480 | 0.347 | −0.411 |
| DBF4 | 0.838 | 0.127 | −0.482 |
| DEF6 | −0.639 | −0.386 | 0.209 |
| DHFR | 0.202 | −0.017 | −0.248 |
| DLL1 | 0.037 | 0.586 | −0.700 |
| DLL3 | 0.277 | 0.755 | −0.649 |
| DNAJC12 | −0.528 | 0.450 | −0.157 |
| DNM3 | 0.005 | 0.914 | −0.497 |
| DPP10 | −0.110 | 0.723 | −0.405 |
| DTL | 0.897 | 0.213 | −0.548 |
| E2F7 | 0.377 | −0.305 | −0.338 |
| ECT2 | 0.818 | 0.382 | −0.485 |
| EFNB2 | 0.241 | −0.582 | 0.441 |
| EMP3 | 0.233 | −0.453 | 0.534 |
| ESM1 | 0.062 | −0.280 | 0.270 |
| EXOSC9 | 0.703 | 0.183 | −0.291 |
| EZH2 | 0.644 | 0.134 | −0.687 |
| FAM20C | −0.185 | −0.718 | 0.357 |
| FANCI | 0.916 | 0.098 | −0.588 |
| FERMT1 | −0.033 | 0.804 | −0.554 |
| FLT1 | −0.003 | −0.071 | 0.117 |
| FOSL2 | −0.178 | −0.410 | 0.583 |
| GABBR1 | 0.180 | 0.700 | −0.329 |
| GALNT13 | −0.456 | 0.903 | −0.315 |
| GGH | 0.697 | 0.039 | −0.585 |
| GGTA1P | −0.509 | 0.205 | 0.219 |

TABLE 4-continued

Extended Nanostring-specific centroids for Phillips expression subtypes

| Gene Symbol | Proliferative | Proneural | Mesenchymal |
|---|---|---|---|
| GINS1 | 1.018 | 0.045 | −0.438 |
| GINS2 | 1.002 | 0.073 | −0.514 |
| GRIA2 | 0.157 | 0.742 | −0.663 |
| HEY2 | 0.040 | 0.468 | −0.324 |
| HMMR | −0.078 | −0.216 | −0.290 |
| ICAM1 | −0.457 | −0.585 | 0.636 |
| KIAA0101 | 0.954 | 0.002 | −0.336 |
| KIAA1244 | −0.048 | 0.855 | −0.334 |
| KLRC3 | 0.068 | 0.794 | −0.486 |
| LIF | −0.222 | −0.657 | 0.638 |
| MELK | 0.610 | −0.144 | −0.506 |
| MYL9 | −0.390 | −0.464 | 0.653 |
| NCAM1 | 0.289 | 0.959 | −0.670 |
| NDRG2 | 0.179 | 0.670 | −0.397 |
| NRP1 | −0.224 | −0.420 | 0.665 |
| NRP2 | −0.119 | −0.289 | 0.519 |
| OLIG2 | 0.302 | 0.683 | −0.697 |
| OMG | 0.029 | 0.965 | −0.584 |
| PCNA | 0.890 | −0.021 | −0.320 |
| PDGFA | 0.605 | −0.390 | −0.060 |
| PDK1 | −0.043 | 0.040 | −0.117 |
| PDLIM4 | −0.132 | −0.362 | 0.190 |
| PDPN | 0.139 | −0.276 | 0.399 |
| PI3 | −0.515 | −0.499 | 0.387 |
| PKNOX2 | −0.236 | 0.144 | −0.400 |
| PLA2G5 | −0.191 | −0.571 | 0.187 |
| PRKCZ | −0.164 | 0.878 | −0.581 |
| PTGDS | −0.474 | 0.583 | 0.031 |
| RASL10A | 0.001 | 0.608 | −0.281 |
| RBM24 | −0.202 | −0.122 | −0.231 |
| RGCC | −0.031 | 0.606 | −0.171 |
| RHOJ | 0.614 | −0.577 | 0.054 |
| RTN1 | 0.037 | 0.557 | −0.228 |
| RYR3 | 0.236 | −0.106 | 0.181 |
| S100A11 | −0.413 | −0.496 | 0.725 |
| SCD | −0.001 | 0.406 | −0.052 |
| SCG3 | 0.210 | 0.612 | −0.432 |
| SERPINA1 | −0.725 | −0.459 | 0.560 |
| SERPINE1 | −0.300 | −0.530 | 0.709 |
| SERPINH1 | −0.045 | −0.643 | 0.614 |
| SMC4 | 0.787 | 0.068 | −0.488 |
| SNAP91 | −0.417 | 0.623 | −0.446 |
| SOX8 | 0.378 | 0.760 | −0.772 |
| SPOCD1 | −0.306 | −0.580 | 0.669 |
| STEAP3 | −0.201 | −0.508 | 0.421 |
| SUSD5 | −0.521 | 0.475 | −0.327 |
| TAGLN | −0.194 | −0.383 | 0.580 |
| TIMP1 | −0.281 | −0.577 | 0.794 |
| TMEM100 | 0.037 | 0.524 | −0.202 |
| TNC | 0.127 | −0.332 | 0.493 |
| TOP2A | 0.928 | 0.284 | −0.555 |
| TRMT6 | 0.693 | 0.126 | −0.249 |
| TTK | 0.822 | 0.113 | −0.561 |
| TYMS | 0.888 | 0.099 | −0.536 |
| ZNF367 | 0.693 | 0.091 | −0.599 |

Example 4. Defining a Shrunken-Centroid Subtype Classifier

Shrunken centroids have been shown to often be more accurate than competing methods in classifying novel samples (Tibshirani et al. *PNAS*. 99(10): 6567-6572, 2002). By shrinking the centroids for each class towards the overall centroids (after standardizing by the within-class standard deviation for each gene), higher weight is assigned to genes whose expression is stable within samples of the same class. At the same time, a reduced set of classifier features can be obtained, e.g. by eliminating genes whose weight is shrunken below a user defined threshold. Here, we have used the PAMR algorithm to obtain a shrunken centroid classifier distinguishing PN from non-PN samples from the AvaGlio Trial.

As described in Example 3, subtype labels were obtained by unsupervised analysis of the preprocessed AvaGlio gene expression data. As a training set for the PAMR algorithm, we combined non-PN samples (Proliferative or Mesenchymal samples) into a single non-PN category (Table 5).

TABLE 5

Number of AvaGlio samples per class used for training of a shrunken centroids classifier (IDH1 wildtype patients only, n = 339)

| Non-Proneural | Proneural |
|---|---|
| 252 | 87 |

Figure 3:
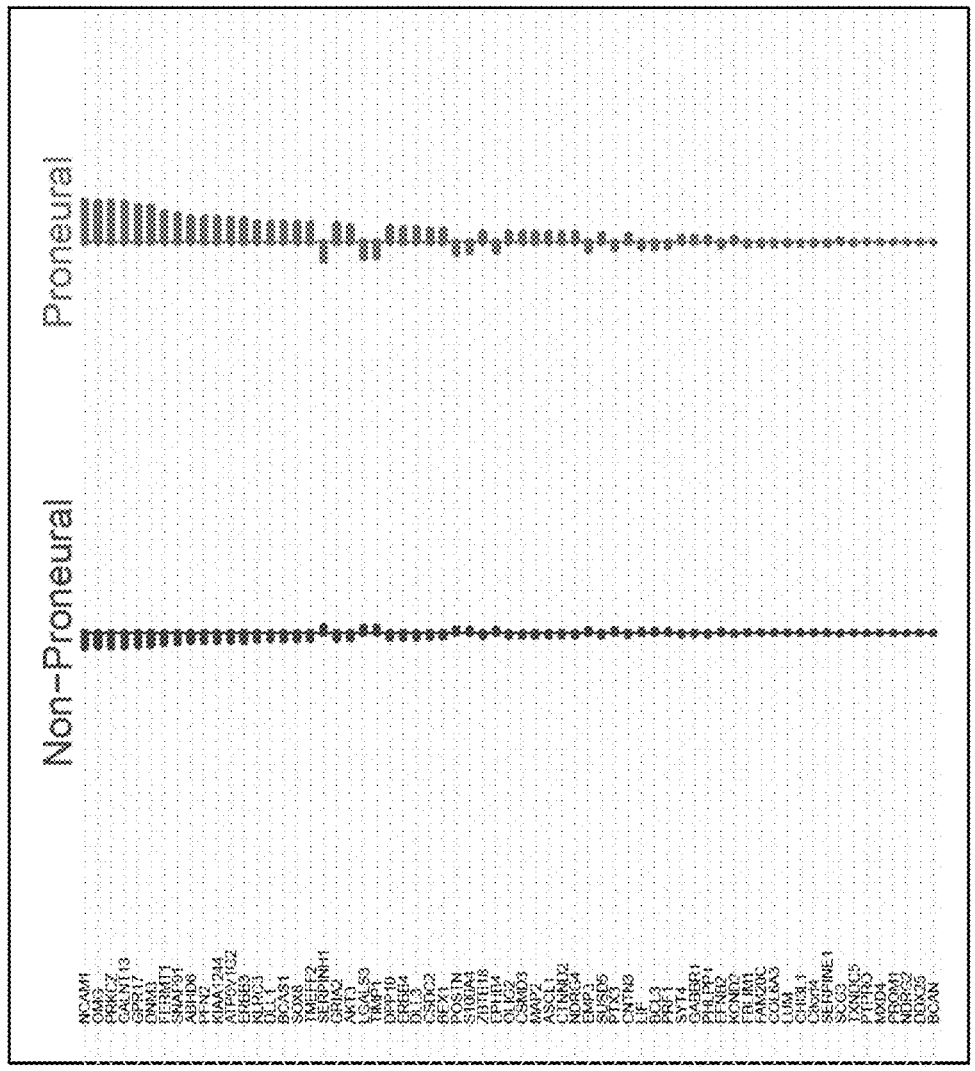
FIG. 3 shows the shrunken centroids obtained with the PAMR algorithm (threshold value=4). Gene-wise scores are shown for the Non-PN and PN centroids. Lines pointed to the left and right indicate negative and positive gene scores, respectively. Line length indicates the magnitude of the gene-wise weight contributed by each to the centroid.

Shrunken centroids were trained using all expression data from all 753 unique genes assayed on the Nanostring platform as input. Class-wise error rates were estimated using 10-fold cross-validation. Here, we chose a shrinkage threshold of 4.0, selecting 65 classifier genes and achieving a mean classification error rate of 9% (see Table 6 and FIG. 3).

TABLE 6

Shrunken centroid classifier obtained with the PAMR algorithm

| Gene Symbol | Non-Proneural-score | Proneural-score |
|---|---|---|
| NCAM1 | −0.0716 | 0.2075 |
| OMG | −0.0698 | 0.2023 |
| PRKCZ | −0.0696 | 0.2016 |
| GALNT13 | −0.0673 | 0.1948 |
| GPR17 | −0.0621 | 0.18 |
| DNM3 | −0.0614 | 0.178 |
| FERMT1 | −0.0508 | 0.1473 |
| SNAP91 | −0.0475 | 0.1376 |
| ABHD6 | −0.0427 | 0.1237 |
| PFN2 | −0.0412 | 0.1194 |
| KIAA1244 | −0.0408 | 0.1181 |
| ATP6V1G2 | −0.0401 | 0.1161 |
| ERBB3 | −0.0399 | 0.1155 |
| KLRC3 | −0.0333 | 0.0965 |
| DLL1 | −0.0326 | 0.0944 |
| BCAS1 | −0.0325 | 0.0943 |
| SOX8 | −0.0324 | 0.0938 |
| TMEFF2 | −0.0322 | 0.0932 |
| SERPINH1 | 0.0316 | −0.0914 |
| GRIA2 | −0.0312 | 0.0902 |
| AKT3 | −0.0266 | 0.0771 |
| LGALS3 | 0.0263 | −0.0762 |
| TIMP1 | 0.0252 | −0.0729 |
| DPP10 | −0.0246 | 0.0712 |
| ERBB4 | −0.0231 | 0.0669 |
| DLL3 | −0.0219 | 0.0634 |
| CSDC2 | −0.0205 | 0.0593 |
| BEX1 | −0.02 | 0.0579 |
| POSTN | 0.0193 | −0.0559 |
| S100A4 | 0.0167 | −0.0484 |
| ZBTB18 | −0.0161 | 0.0468 |
| EPHB4 | 0.0159 | −0.046 |
| OLIG2 | −0.0157 | 0.0455 |
| CSMD3 | −0.0152 | 0.0441 |
| MAP2 | −0.0149 | 0.0432 |
| ASCL1 | −0.0147 | 0.0426 |
| CTNND2 | −0.0142 | 0.0412 |
| NDRG4 | −0.014 | 0.0405 |
| EMP3 | 0.014 | −0.0405 |
| SUSD5 | −0.0131 | 0.038 |
| PTX3 | 0.011 | −0.032 |
| CNTN3 | −0.0109 | 0.0315 |
| LIF | 0.0101 | −0.0292 |
| BCL3 | 0.0096 | −0.0279 |
| PRF1 | 0.0082 | −0.0237 |
| SYT4 | −0.0076 | 0.0221 |
| GABBR1 | −0.0071 | 0.0205 |
| PHLPP1 | −0.0069 | 0.0199 |
| EFNB2 | 0.0068 | −0.0196 |

TABLE 6-continued

Shrunken centroid classifier obtained with the PAMR algorithm

| Gene Symbol | Non-Proneural-score | Proneural-score |
|---|---|---|
| KCND2 | −0.0057 | 0.0165 |
| FBLIM1 | 0.0053 | −0.0153 |
| FAM20C | 0.0045 | −0.0131 |
| COL6A3 | 0.0045 | −0.013 |
| LUM | 0.0036 | −0.0104 |
| CHI3L1 | 0.0035 | −0.01 |
| C8orf4 | 0.0034 | −0.01 |
| SERPINE1 | 0.003 | −0.0086 |
| SCG3 | −0.0029 | 0.0083 |
| TXNDC5 | 0.0015 | −0.0042 |
| PTPRO | −5.00E−04 | 0.0014 |
| MXD4 | −4.00E−04 | 0.0013 |
| PROM1 | −3.00E−04 | 0.001 |
| NDRG2 | −3.00E−04 | 9.00E−04 |
| DDX25 | −1.00E−04 | 3.00E−04 |
| BCAN | −1.00E−04 | 2.00E−04 |

To test the performance of the shrunken centroid classifier on the training data, we re-classified all AvaGlio samples into PN or non-PN subgroups based on the posterior class probabilities assigned by PAMR. We observed good performance of the classifier on the training data (91% recall) and assigned 71 samples to the PN subgroup.

Figure 4:
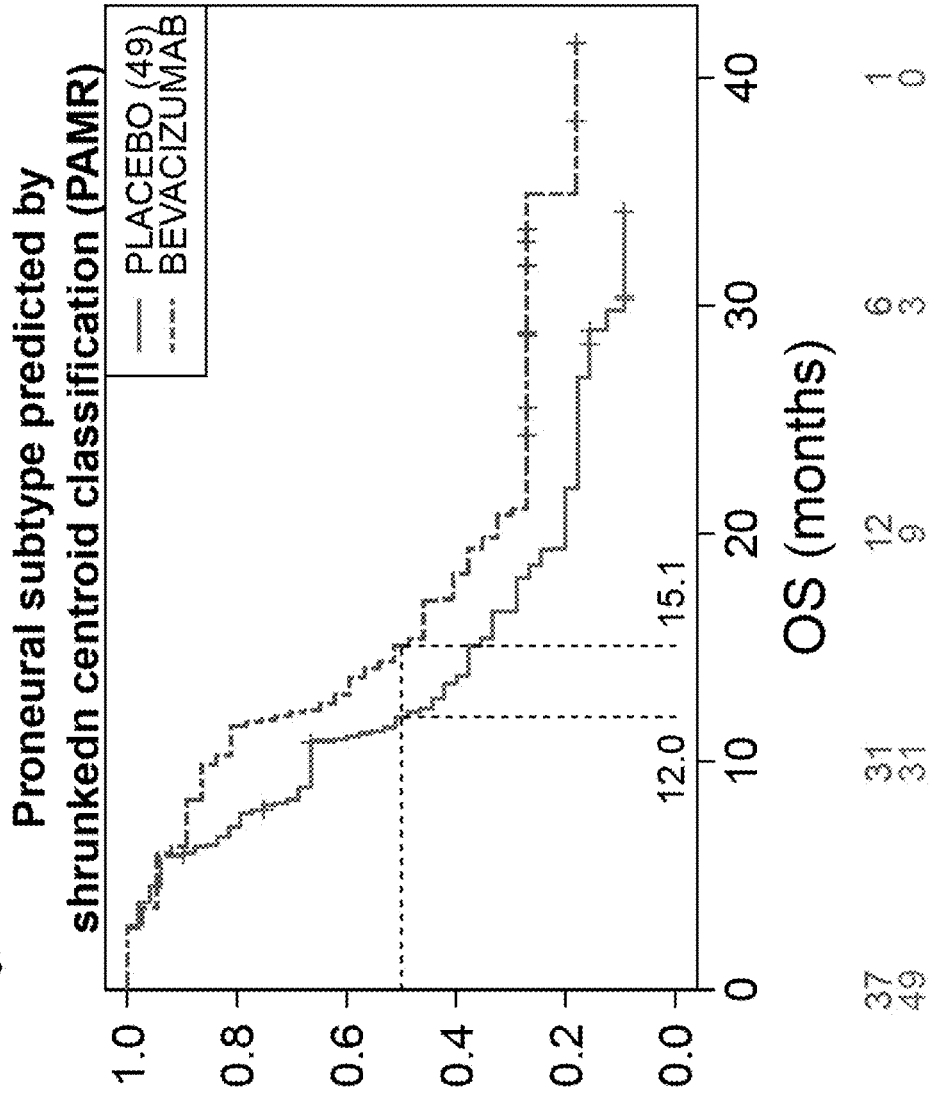
FIG. 4 is a Kaplan-Meier survival curve of patients assigned to the Proneural (PN) subtype using shrunken centroid classification (PAMR) in the two AvaGlio treatment arms (bevacizumab treatment arm: dashed line; placebo treatment arm: solid line). The number of patients at risk is indicated below the graph for the bevacizumab treatment (top row) and placebo treatment arms (bottom row).

To test for the predictive value of this subgroup classification result, we performed a multivariate analysis of the effect of anti-VEGF therapy (e.g., anti-VEGF antibody therapy, e.g., bevacizumab therapy) in combination with RT and chemotherapy on OS in this subgroup, accounting for the main known clinical covariates (e.g., age, corticosteroids, extent of resection, gender, Karnofsky Performance Score (KPS), methylation status of O-6-methylguanine-DNA methyltransferase (MGMT) promoter, mini-mental state examination score (MMSE), recursive partitioning analysis (RPA) class, and WHO performance score)). The multivariate Cox PH indicates that anti-VEGF therapy resulted in a significant OS benefit for patients having PN subtype glioblastoma, but not for patients having non-PN subtype glioblastoma (FIG. 4). Specifically, for patients having PN subtype glioblastoma, median OS in the treatment arm was 15.1 months compared to 12.0 months in the placebo arm, with a HR equal to 0.42 (95% CI=0.24-0.75; p=0.003).

Example 5. Deriving a Continuous Predictive Proneural Score

In previous examples, we have demonstrated that patients can be classified into gene expression subtypes and that assignment to the Proneural (PN) subtype is predictive for anti-VEGF therapy (e.g., anti-VEGF antibody therapy, e.g., bevacizumab therapy) in combination with RT and chemotherapy on OS in this subgroup. Here, we used the top ten most highly weighted predictor genes from the shrunken centroid classifier (Example 4) to calculate a quantitative PN score for each patient.

The following ten genes discriminated best between PN and non-PN samples according to the PAMR algorithm (Table 6) and received the largest scores: NCAM1, OMG, PRKCZ, GALNT13, GPR17, DNM3, FERMT1, SNAP91, ABHD6 and PFN2. All of these genes show higher relative expression in PN samples than in non-PN samples (Table 6). We therefore summarized their expression by calculating the mean z-score across all ten genes for each patient in the AvaGlio biomarker available population (IDH1 wildtype patients only; n=339).

Figure 5:
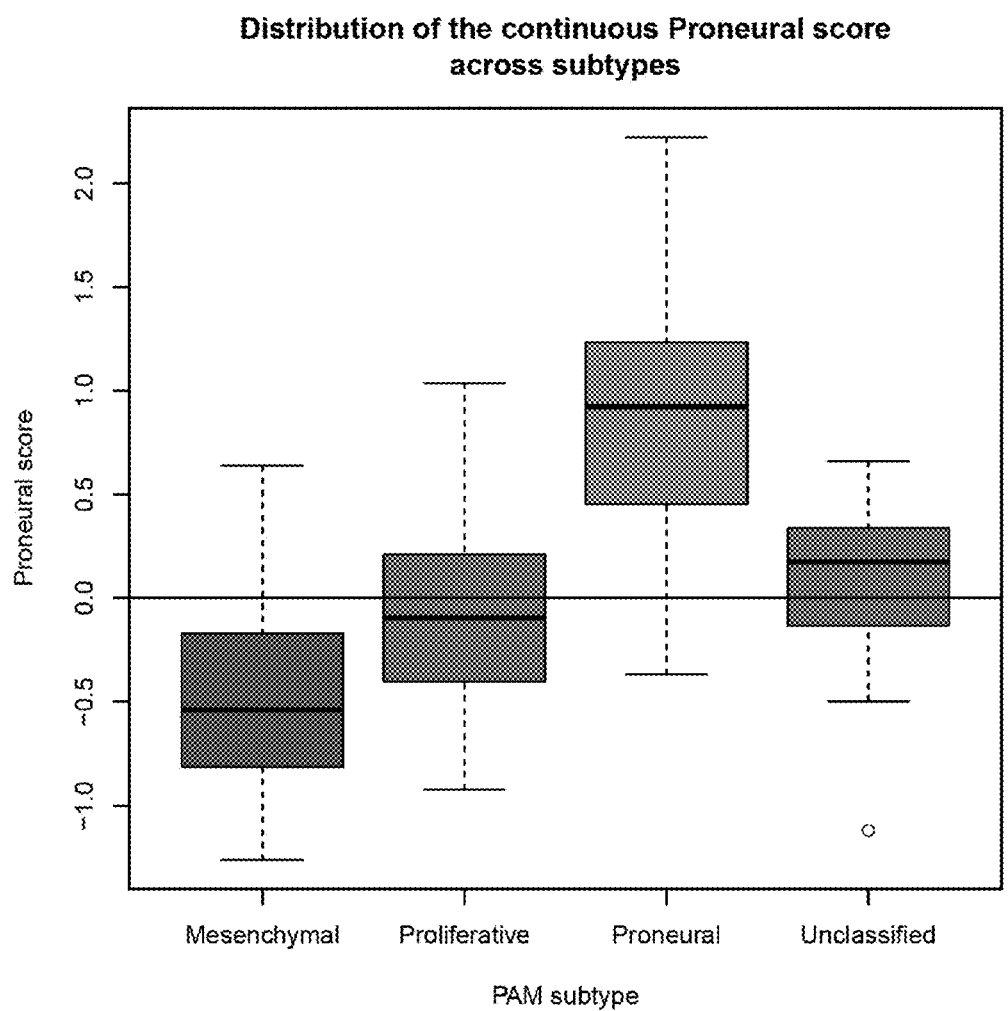
FIG. 5 is a boxplot showing the distribution of the continuous Proneural score across the subtypes identified by unsupervised analysis (PAM). The Proneural score was calculated as the mean z-score across the following ten genes for each patient: NCAM1, OMG, PRKCZ, GALNT13, GPR17, DNM3, FERMT1, SNAP91, ABHD6 and PFN2.

As expected, this continuous summary score is highly correlated with the Phillips' gene expression subtype assignment derived from an unsupervised analysis (PAM, Example 3). Patients classified as "Proneural" showed high continuous Proneural scores, patients classified as "Mesenchymal" showed low continuous Proneural scores, and patients classified as "Proliferative" showed intermediate scores (FIG. 5).

To test for the predictive value of this continuous Proneural score, we performed a multivariate analysis of the effect of anti-VEGF therapy (e.g., anti-VEGF antibody therapy, e.g., bevacizumab therapy) in combination with RT and chemotherapy on OS for the complete biomarker available population (IDH1 wildtype patients; n=339), accounting for the main known clinical covariates (e.g., age, corticosteroids, extent of resection, gender, Karnofsky Performance Score (KPS), methylation status of O-6-methylguanine-DNA methyltransferase (MGMT) promoter, mini-mental state examination score (MMSE), recursive partitioning analysis (RPA) class, and WHO performance score)), The multivariate Cox PH indicates both significant prognostic (p=0.004 for the biomarker main effect) and predictive (p=0.005 for the treatment/biomarker interaction effect) value of the continuous Proneural score.

Figure 6A:
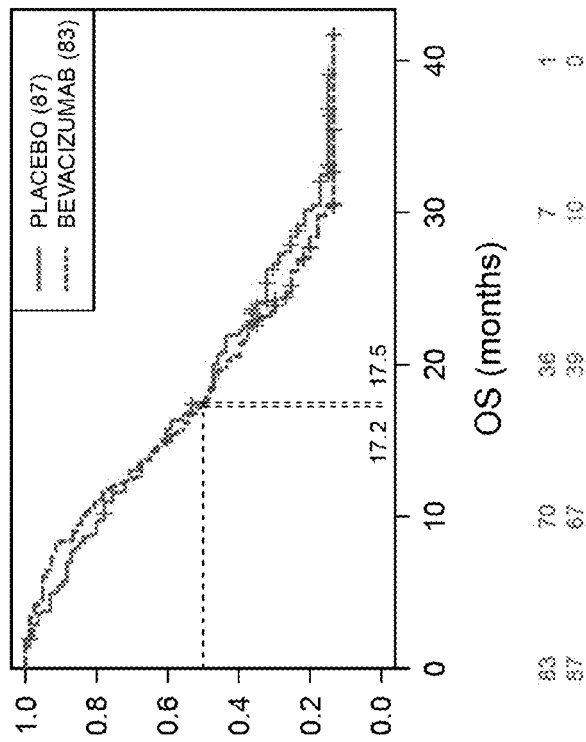
FIG. 6A is a Kaplan-Meier survival curve of patients in the two AvaGlio treatment arms (bevacizumab treatment arm: dashed line; placebo treatment arm: solid line) assigned to the "biomarker-high" subgroup, based on splitting the continuous Proneural score at the median. The number of patients at risk is indicated below the graph for the bevacizumab treatment (top row) and placebo treatment arms (bottom row).
Figure 6B:
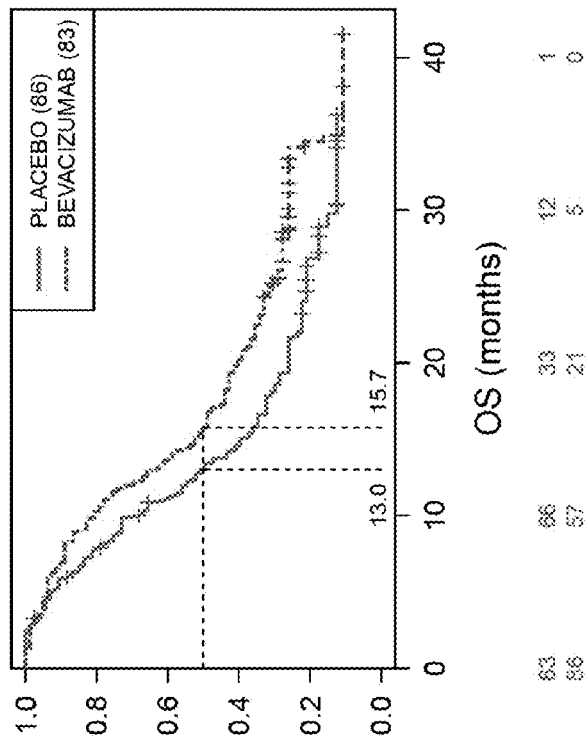
FIG. 6B is a Kaplan-Meier survival curve of patients in the two AvaGlio treatment arms (bevacizumab treatment arm: dashed line; placebo treatment arm: solid line) assigned to the "biomarker-low" subgroup, based on splitting the continuous Proneural score at the median. The number of patients at risk is indicated below the graph for the bevacizumab treatment (top row) and placebo treatment arms (bottom row).

To visualize the predictive value of the continuous Proneural score, we dichotomized the patients into a "biomarker low" and "biomarker high" population by splitting at the median continuous Proneural score (e.g. separating the 50% of the patients with the highest and lowest scores, respectively). As shown in FIG. 6A, for patients in the "biomarker-high" subgroup, median OS in the treatment arm was 15.7 months compared to 13.0 months in the placebo arm, with a HR equal to 0.51 (95% CI=0.35-0.75; p=0.0006, multivariate CoxPH fit within the biomarker-high population). No significant difference between treatment arms was observed for the "biomarker-low" population (FIG. 6B).

Although the foregoing invention has been described in some detail by way of illustration and example for purposes of clarity of understanding, the descriptions and examples should not be construed as limiting the scope of the invention. The disclosures of all patents, patent applications, scientific references, and Genbank Accession Nos. cited herein are expressly incorporated by reference in their entirety for all purposes as if each patent, patent application, scientific reference, and Genbank Accession No. were specifically and individually incorporated by reference.

What is claimed is:

1. A method of treating a patient having a proneural subtype glioblastoma who is likely to respond to treatment with an anti-VEGF antibody, the method comprising:
    (a) detecting expression of at least one of the genes set forth in Table 1, 2, or 3 in a biological sample obtained from the patient prior to administration of the anti-VEGF antibody to the patient;
    (b) comparing the expression level of the at least one gene to a reference expression level of the at least one gene, wherein a change in the level of expression of the at least one gene in the patient sample relative to the reference expression level identifies the patient as one who has a glioblastoma of the proneural subtype and is likely to respond to treatment with the anti-VEGF antibody; and
    (c) administering an effective amount of the anti-VEGF antibody to the patient identified as likely to respond to treatment with the anti-VEGF antibody.

2. The method of claim 1, wherein the reference expression level is the median level of expression of the at least one gene in a population of patients having glioblastomas.

3. The method of claim 1, wherein the reference expression level is the median level of expression of the at least one gene in patients having glioblastomas and identified as not responding to anti-VEGF antibody treatment.

4. The method of claim 1, wherein the change in level of expression of the at least one gene in the patient sample is an increase relative to the reference level.

5. The method of claim 1, wherein the change in level of expression of the at least one gene in the patient sample is a decrease relative to the reference level.

6. The method of claim 1, further comprising detecting expression of at least two of said genes in the biological sample from the patient.

7. The method of claim 1, wherein the administered anti-VEGF antibody is bevacizumab.

8. The method of claim 1, wherein the administered anti-VEGF antibody comprises a variable heavy chain (VH) and a variable light chain (VL), wherein said VH has an amino acid sequence of SEQ ID NO: 2 and said VL has an amino acid sequence of SEQ ID NO: 1.

9. The method of claim 1, further comprising administering an effective amount of at least a second agent.

10. The method of claim 9, wherein the second agent is selected from the group consisting of: an anti-neoplastic agent, a chemotherapeutic agent, a growth inhibitory agent, and a cytotoxic agent, or combinations thereof.

11. The method of claim 1, wherein responsiveness to treatment with the anti-VEGF antibody is an increase in overall survival.

12. The method of claim 1, wherein the at least one gene is selected from the group consisting of NCAM1, OMG, PRKCZ, GALNT13, GPR17, DNM3, FERMT1, SNAP91, ABHD6, and PFN2.

13. The method of claim 12, wherein the change in level of expression of the at least one gene in the patient sample is an increase relative to the reference level.

14. A method of treating a patient having a proneural subtype glioblastoma who is likely to respond to treatment with an anti-VEGF antibody, the method comprising:

(a) detecting expression of at least one gene in a biological sample obtained from the patient prior to administration of the anti-VEGF antibody to the patient, wherein the at least one gene is selected from the group consisting of NCAM1, OMG, PRKCZ, GALNT13, GPR17, DNM3, FERMT1, SNAP91, ABHD6, and PFN2;

(b) comparing the expression level of the at least one gene to a reference expression level of the at least one gene, wherein an increase in the level of expression of NCAM1, OMG, PRKCZ, GALNT13, GPR17, DNM3, FERMT1, SNAP91, ABHD6, and/or PFN2 in the patient sample relative to the reference expression level identifies the patient as one who has a glioblastoma of the proneural subtype and is likely to respond to treatment with the anti-VEGF antibody; and (c) administering an effective amount of the anti-VEGF antibody to the patient identified as likely to respond to treatment with the anti-VEGF antibody.

\* \* \* \* \*

SEQUENCE LISTING

<160> NUMBER OF SEQ ID NOS: 2

<210> SEQ ID NO 1
<211> LENGTH: 108
<212> TYPE: PRT
<213> ORGANISM: Artificial Sequence

```
<220> FEATURE:
<223> OTHER INFORMATION: Synthetic Construct

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg
            100                 105

<210> SEQ ID NO 2
<211> LENGTH: 123
<212> TYPE: PRT
<213> ORGANISM: Artificial Sequence
<220> FEATURE:
<223> OTHER INFORMATION: Synthetic Construct

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
            115                 120
```